(12) United States Patent
Collins

(10) Patent No.: US 11,958,050 B2
(45) Date of Patent: Apr. 16, 2024

(54) FLUIDIC DEVICES FOR CLOSED CELL CULTURE APPLICATIONS UNDER CURRENT GOOD MANUFACTURING PRACTICE

(71) Applicant: John Collins, Irvine, CA (US)

(72) Inventor: John Collins, Irvine, CA (US)

( * ) Notice: Subject to any disclaimer, the term of this patent is extended or adjusted under 35 U.S.C. 154(b) by 1118 days.

(21) Appl. No.: 16/418,672

(22) Filed: May 21, 2019

(65) Prior Publication Data

US 2019/0358633 A1    Nov. 28, 2019

Related U.S. Application Data

(60) Provisional application No. 62/675,841, filed on May 24, 2018.

(51) Int. Cl.
| | |
|---|---|
| *C12M 3/00* | (2006.01) |
| *B01L 3/00* | (2006.01) |
| *C12M 1/00* | (2006.01) |
| *C12M 1/34* | (2006.01) |

(52) U.S. Cl.
CPC ... *B01L 3/502761* (2013.01); *B01L 3/502715* (2013.01); *B01L 3/50273* (2013.01); *B01L 3/502738* (2013.01); *C12M 23/34* (2013.01); *C12M 29/10* (2013.01); *C12M 41/12* (2013.01); *B01L 2200/0668* (2013.01); *B01L 2300/0681* (2013.01); *B01L 2400/0415* (2013.01); *B01L 2400/049* (2013.01)

(58) Field of Classification Search
CPC ...... C12M 27/16; C12M 29/10; C12M 29/00; C12M 41/12; B01L 2300/0645; B01L 3/502761; B01L 3/502715; B01L 3/50273; B01L 3/502738; B01L 2200/0668; B01L 2300/0681; B01L 2400/0415; B01L 2400/049
See application file for complete search history.

(56) References Cited

U.S. PATENT DOCUMENTS

| | | | | |
|---|---|---|---|---|
| 6,096,532 | A  * | 8/2000 | Armstrong | C12M 23/54 435/284.1 |
| 2011/0287529 | A1* | 11/2011 | Hong | C12M 27/10 435/288.1 |
| 2014/0030752 | A1* | 1/2014 | Cuiffi | C12M 23/12 435/375 |
| 2016/0002584 | A1* | 1/2016 | Nozaki | C12M 21/08 435/289.1 |
| 2016/0264918 | A1* | 9/2016 | Shimase | C12M 29/00 |
| 2016/0355773 | A1* | 12/2016 | Kurakazu | C12M 25/06 |

(Continued)

*Primary Examiner* — Brian J. Sines

(57) ABSTRACT

A system and method for automated and closed cell culture system. The system includes a disposable assembly, actuators, sensors, software/firmware and smart device App. The disposable includes fresh media, drug or reagents containers, waste container, sample out containers, cell culture flask, well, bag or bioreactor and active or passive pumping elements. The system is expanded to multiple containers cell or organ processing. In all these precisely controlling the fluids are achieved by interdigitated differential capacitance measurements. The system has provision for imaging, machine vision control, controlled over the internet, volume metering and can use wide variety of pumps for actuation. The system is programmed to perform cGMP protocols and operated as a portable instrument.

14 Claims, 27 Drawing Sheets

(56) References Cited

U.S. PATENT DOCUMENTS

| | | | |
|---|---|---|---|
| 2017/0058252 A1* | 3/2017 | Zhang | C12M 23/14 |
| 2017/0067019 A1* | 3/2017 | Ho | C12N 5/063 |
| 2018/0282682 A1* | 10/2018 | Pebay | C12M 41/48 |
| 2018/0371394 A1* | 12/2018 | Ho | C12M 29/24 |
| 2019/0078044 A1* | 3/2019 | Ohkubo | C12M 3/00 |
| 2019/0352589 A1* | 11/2019 | Jing | C12M 25/10 |

* cited by examiner

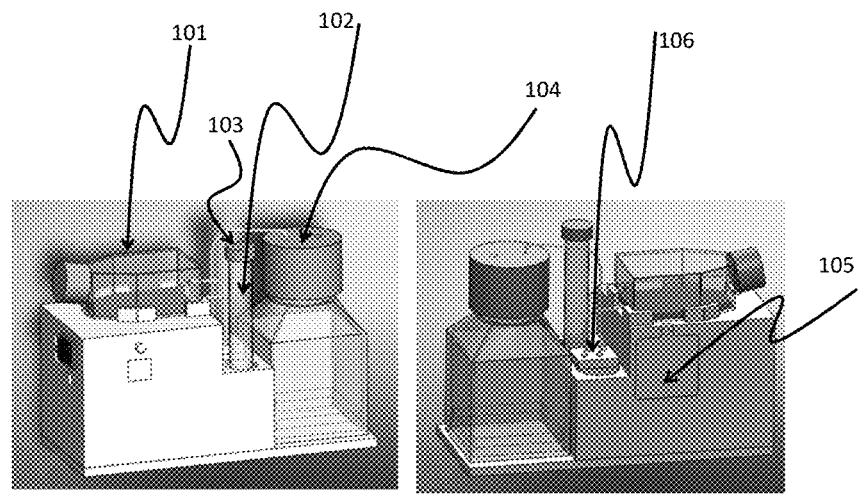
Fig. 1A
Fig. 1B
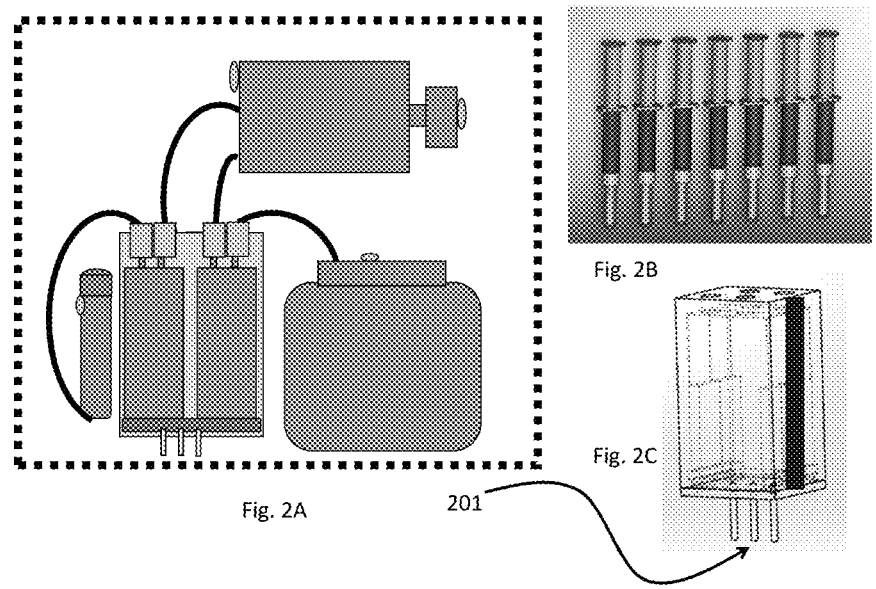
Fig. 2A
Fig. 2B
Fig. 2C

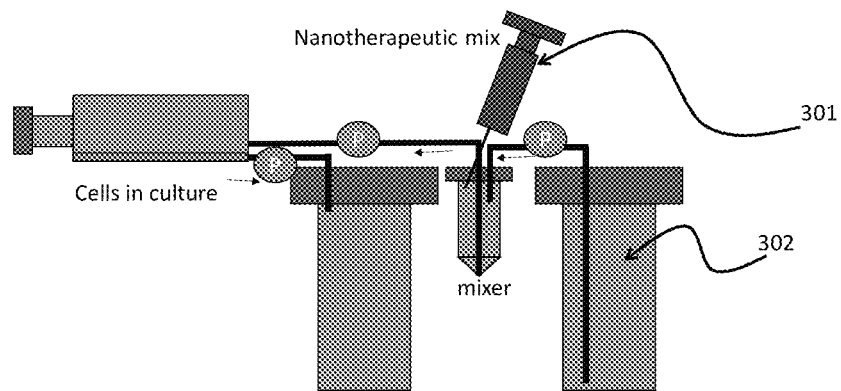
Fig. 3
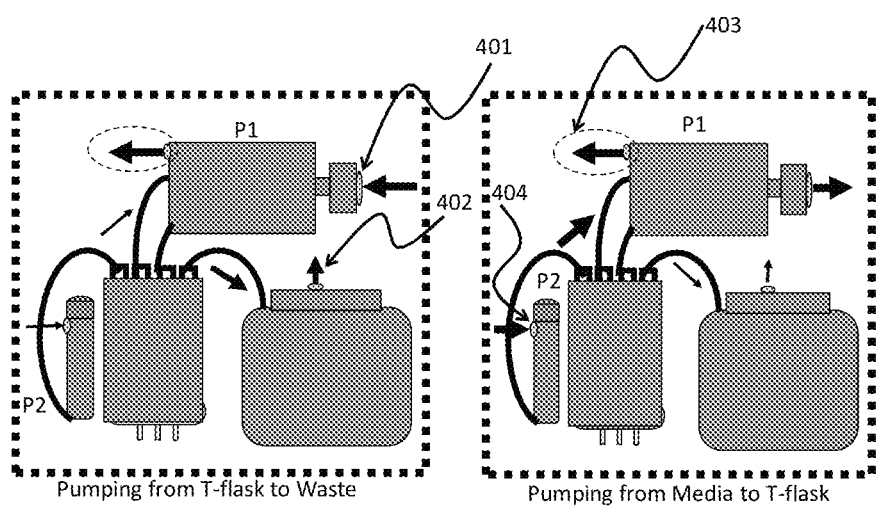
Fig. 4A
Fig. 4B

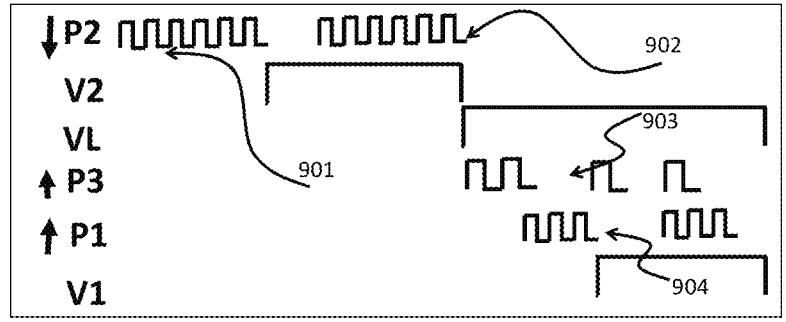

Fig. 9A

1. Stepper UP
2. P2 Vacuum pump (vacuum boost)
3. V2 Valve ON (bubble clear)
4. P2 Vacuum pump pulse (waste pull)
5. V2 valve OFF
6. VL valve ON (vent)
7. P3 pulse (vent)
8. Stepper DOWN
9. P1 pressure pump (pressure boost)
10. V1 valve ON (bubble clear)
11. P2 Pressure pump pulse; P3 pulse
12. V1, VL Valves OFF

Fig. 9B

1. Load cell/media
2. Place in incubator
3. Turn Power ON
4. Next Day Inject 3ml media
5. Press Switch
6. Indicator one blink
7. Wait 20minutes to warm up media
8. Tilt the T-flask
9. Waste removal in steps
10. Restore the T-flask position
11. Fresh Media addition in steps
12. Wait till next day / Goto 4

Fig. 10A

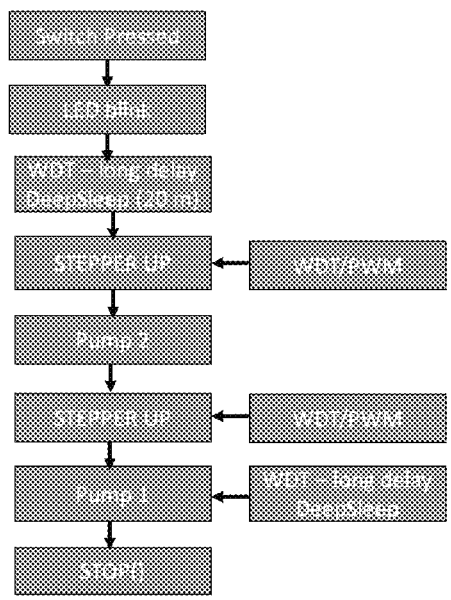

Fig. 10B

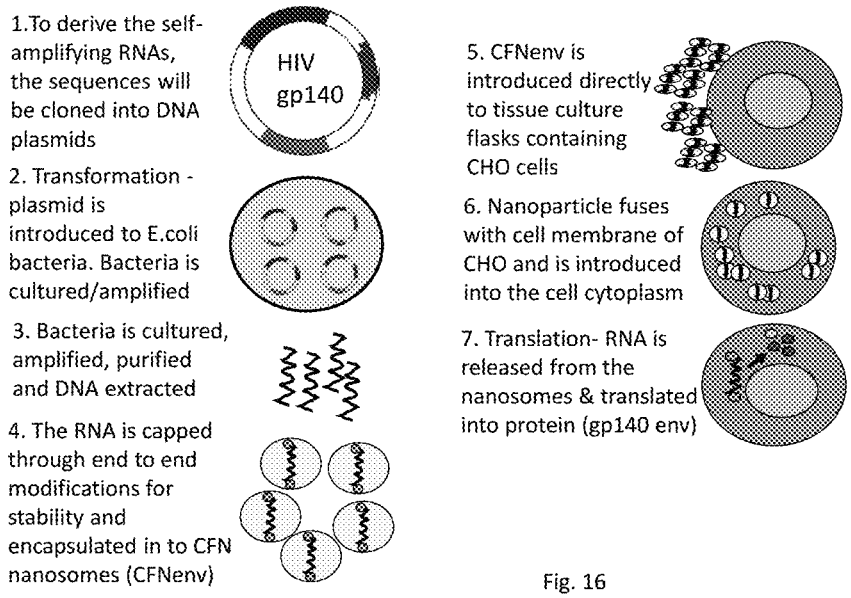
Fig. 16
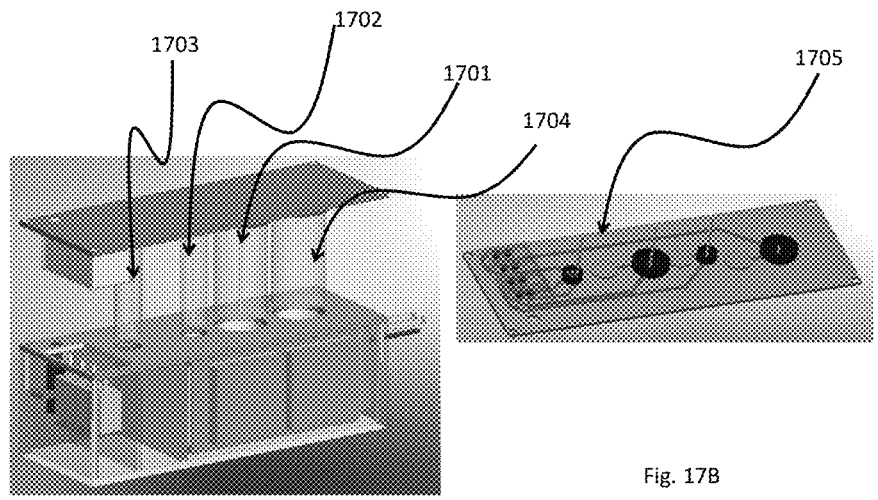
Fig. 17A
Fig. 17B

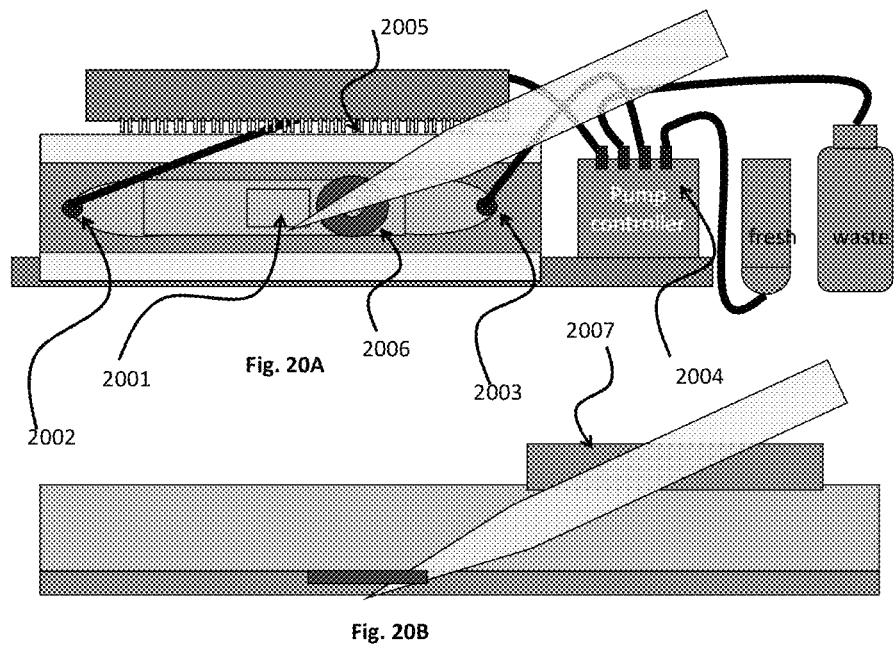
Fig. 20A
Fig. 20B
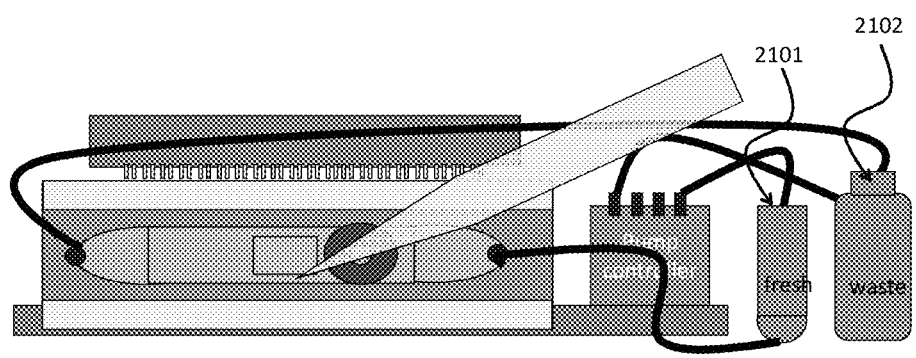
Fig. 21

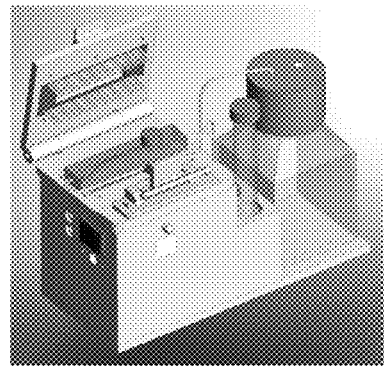
Fig. 22A
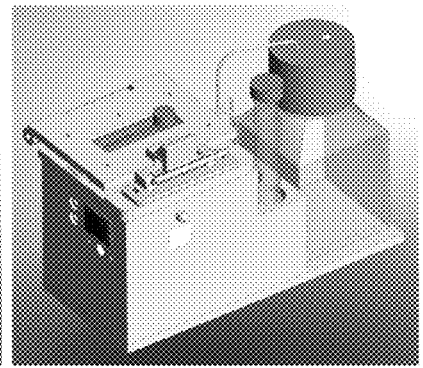
Fig. 22B
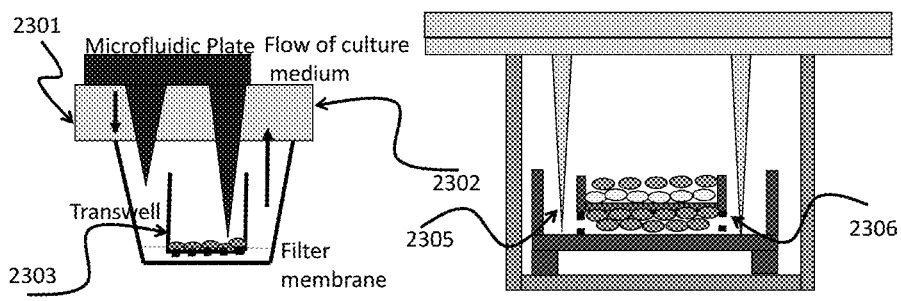
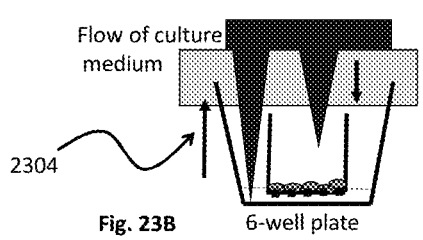
Fig. 23B
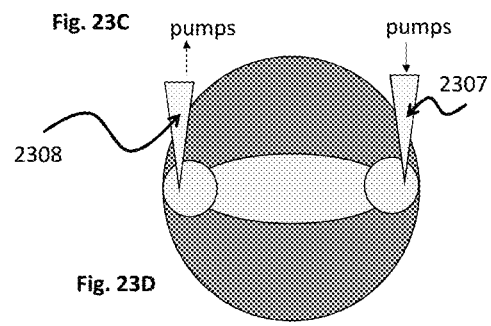
Fig. 23D

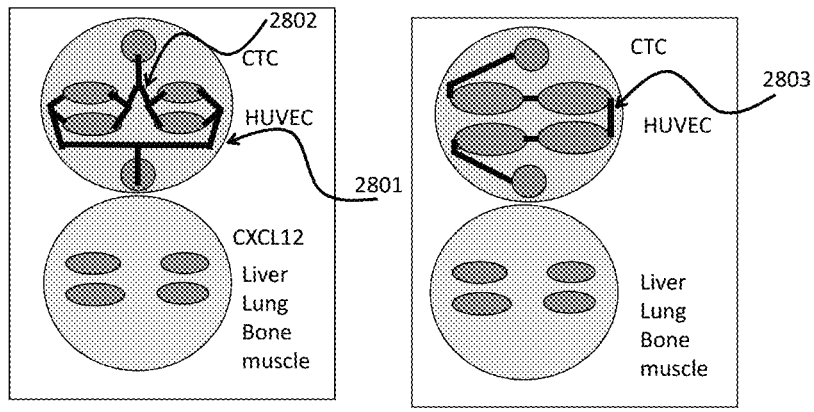
Fig. 28A
Fig. 28B
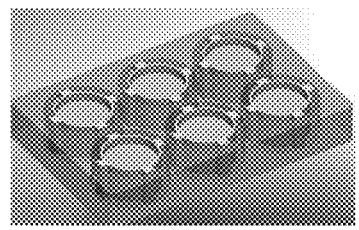
Fig. 28C
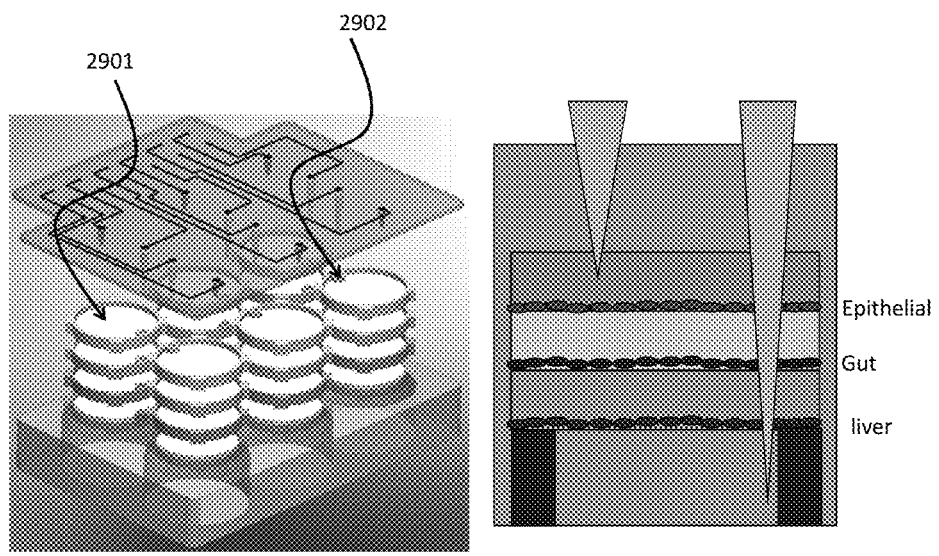
Fig. 29A
Fig. 29B

Gear pump

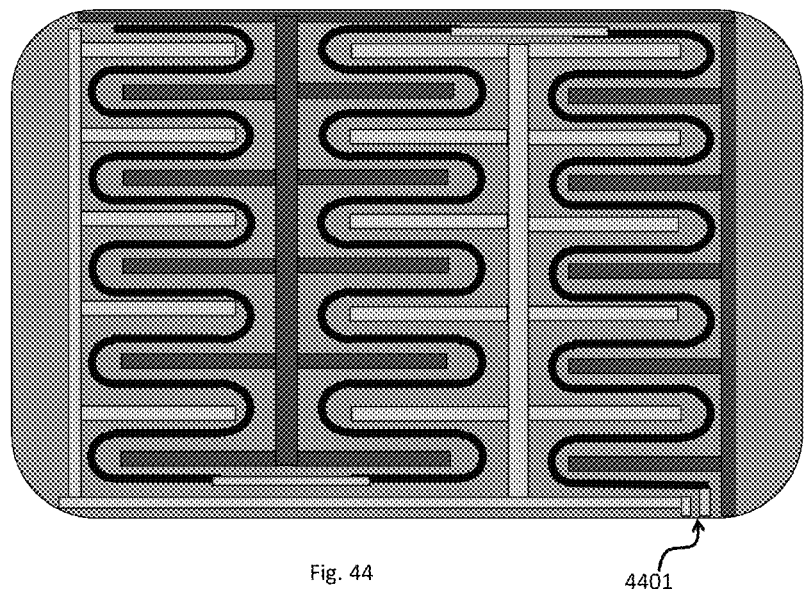
Fig. 44      4401
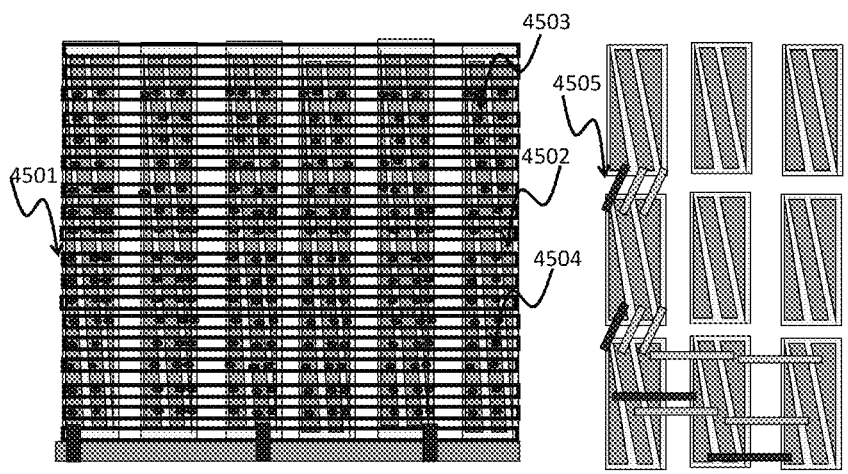
Fig. 45A      Fig. 45B
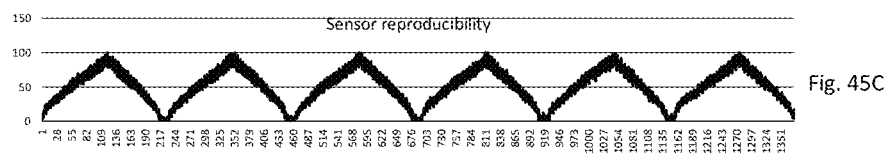
Fig. 45C Machine Vision control for Media Change

FLUIDIC DEVICES FOR CLOSED CELL CULTURE APPLICATIONS UNDER CURRENT GOOD MANUFACTURING PRACTICE

CROSS-REFERENCE TO RELATED APPLICATIONS

The present application claims the benefit of and priority to U.S. Provisional Patent Application titled "Fluidic devices for closed cell culture applications under current Good Manufacturing Practice," Ser. No. 62/675,841, filed on May, 24, 2018. The disclosure in this provisional application is hereby incorporated fully by reference into the present application.

STATEMENT REGARDING FEDERALLY-SPONSORED RESEARCH AND DEVELOPMENT

This invention was made with Government support under contract No. R43MH104170 awarded by the National Institute of Health (NIH). The Government has certain rights in this invention.

FIELD OF THE INVENTION

The present invention generally relates to medical devices and methods, and more particularly to microfluidic devices and methods for closed cell culture in current good manufacturing practice applications.

BACKGROUND OF THE INVENTION

Microfluidic systems provide remarkable features for controlling the fluidics in cell culture for stem cell reprogramming, stem cell therapeutic culture and cell assays. Fluidic circuits can mix two or more reagents, develop multiple composition of reagents, perform concentration gradient and deliver fluids at set intervals in a closed system for cell culture. A portable closed system is important for operations involving current good manufacturing practice. Control of cell media or reagent exchange can be open loop without any feedback or active control with feedback from monitoring the environment, fluids or cells by parameters not limited to optical, electrical, mechanical, chemical and acoustics.

SUMMARY

The present invention is directed to a system and a method for cell culture and cell based assays in a closed system using microfluidics system equipped with micropumps, volume metering, cell imaging/image processing and control systems substantially as shown in and/or described in connection with at least one of the figures, and as set forth more completely in the claims.

In accordance with an aspect of the present invention, there are provided methods for performing media exchange for T-flask, cells in bags, bioreactors, standard well plates, custom wells in a closed fluidics system.

In accordance with another aspect of the present invention, there are provided systems with disposables and non-disposable devices works in conjunction for delivering media, drug or reagents to cells in culture in a closed system from closed containers to above said T-flask, cell bags, bioreactors or wells and remove waste or selected cells or samples to closed containers.

In accordance with yet another aspect of the present invention, there are provided methods for disposables to "plug and play" in the system through electrical contacts for active pumping, sensing or monitoring.

In accordance with yet another aspect of the present invention, there are provided methods to remove used media by tilting the closed cell containers or by forced flow in to waste container In accordance with another aspect of the present invention, there are provided methods for performing concentration gradient using splitting fluidic flow from two or more inputs of drug, growth factor, toxin, stimuli agents, other chemicals or reagents.

In accordance with yet another aspect of the present invention, there are provided methods for performing aliquots of drug or reagents to cells in culture through closed elastic caps by piercing them and still maintaining closed state.

In accordance with yet another aspect of the present invention, there are provided methods to insert disposable using electrical, mechanical or fluidic contacts with the non-disposable system.

In accordance with yet another aspect of the present invention, there are provided methods for preprocessing the reagents in a closed container from multiple reagents from closed containers before transporting to cells in culture.

In accordance with yet another aspect of the present invention, there are provided methods for using hydrophobic filters (pore sizes 0.1 um, 0.2 um, and 0.22 um) release excess pressure while not allowing any contaminants to enter the cells in culture In accordance with yet another aspect of the present invention, there are provided methods for carrying out pumping from media/reagent containers to cell culture container while avoiding any leaking of fluids from the cell container to waste by pumping in pulses and waiting between trains of pulses.

In accordance with yet another aspect of the present invention, there are provided methods for pumping to or from cell culture containers by pressure or vacuum through filters as a closed system so that liquid media or reagents will not contact the pumps and the pumps needed not be disposed after every experiment.

In accordance with yet another aspect of the present invention, there are provided methods for rapid connection of fluidics from disposable to non-disposable system by using a manifold which allow air pressure or vacuum pass through connectors including O-rings.

In accordance with yet another aspect of the present invention, there are provided methods for avoiding backflow by venting the pressure or vacuum through additional valves and pumps in the fluidic paths.

In accordance with yet another aspect of the present invention, there are provided methods for periodic or aperiodic pumping of air across containers with or without monitoring their internal pressures, to keep the pressure balanced for any backflow or contamination from one container to another container.

In accordance with yet another aspect of the present invention, there are provided methods for clearing bubbles formed in the tubing that block the flow, by flushing with boost pressure or vacuum initially.

In accordance with yet another aspect of the present invention, there are provided methods for generating boost pressure or vacuum using another tank and a valve between pump and the reservoir.

In accordance with yet another aspect of the present invention, there are provided methods for timings of pressure pumps and valves to activate in a sequence so that air/vacuum based cell culture reagents are robustly and repeated transported from one container to another.

In accordance with yet another aspect of the present invention, there are provided methods for accomplishing the cell culture system to run on battery power with minimum power consumption using techniques including watchdog timer, deep sleep and long delay generation programming.

In accordance with yet another aspect of the present invention, there are provided methods for pumping multiple media or drug or reagents from multiple containers to cell culture container by multiple pumps.

In accordance with yet another aspect of the present invention, there are provided methods for collecting selected cells or proteins or analytes from cells in culture from a closed container through immunomagnetic magnetic beads by applying magnetic field from permanent magnet or electromagnet.

In accordance with yet another aspect of the present invention, there are provided methods for flow based culture of cells in bags or bioreactors using suspension cell aggregates in compartments separated by filters.

In accordance with yet another aspect of the present invention, there are provided methods for providing homogeneous mixing and supplying fresh media and/or dissolved oxygen/CO2 mixture using overlapping channels and alternative pulsed pumping of media in to the cell culture.

In accordance with yet another aspect of the present invention, there are provided methods for culturing adherent cells on filters or mesh placed within cell bags attached to a tray.

In accordance with yet another aspect of the present invention, there are provided methods for transporting cells in cell culture compartmental bags under perfusion with media reservoir, integrated electronics and batteries.

In accordance with yet another aspect of the present invention, there are provided methods for performing continuous cell culture, cell differentiation and cell assays with reagents including cell media, growth factor and differentiation buffer within the incubator at 37 deg C. while storing at 4 deg C. inside the incubator so that such reagents can be used in the cell culture container on demand.

In accordance with yet another aspect of the present invention, there are provided methods for producing proteins from cells in culture after packaging molecular transcripts in nanoparticles and releasing into the cells.

In accordance with yet another aspect of the present invention, there are provided methods for performing multistep molecular assays including transformation, amplification purification, encapsulation, introduction, fusion and translation for continuous cell culture.

In accordance with yet another aspect of the present invention, there are provided methods for plugging a lid for multiple reservoirs, manifold and pumping element while storing in very low temperature including 4 deg C.

In accordance with yet another aspect of the present invention, there are provided to control the temperature in the incubator at very low temperature including 4 deg C. using one or more thermoelectric coolers and providing shutdown under safety conditions.

In accordance with yet another aspect of the present invention, there are provided cooling thermoelectric elements using circulation of water or coolants using pump, radiator, fan and controlled using feedback sensors.

In accordance with yet another aspect of the present invention, there are provided methods for delivering cells in closed chamber chips and performing media exchange into the chamber from external fresh media containers.

In accordance with yet another aspect of the present invention, there are provided methods to deliver cells into cell culture chip through a hole outside the viewing area of the cells and delivery into wells in the chip at an angle through the hole.

In accordance with yet another aspect of the present invention, there are provided methods to connect electrical pins for further processing electrical signals including field potential signals and impedance signals and fluidic ports for supplying media or reagents to the cells.

In accordance with yet another aspect of the present invention, there are provided methods to deliver media or reagents through transwell insert membrane from top to bottom or bottom to top using one or more inner wells for one or more cells within the wells.

In accordance with yet another aspect of the present invention, there are provided methods to deliver fluids to transwell inserts through a well and receive fluids from transwell insert through another well within the transwell insert.

In accordance with yet another aspect of the present invention, there are provided methods to transport flesh media from one well to other wells of well plate and also to collect used media from the wells to a well.

In accordance with yet another aspect of the present invention, there are provided methods to transport fresh media from outside to the designated fresh media well and also to remove the used media from the designated waste media well.

In accordance with yet another aspect of the present invention, there are provided methods to carry out organs system culture with interacting organs from multiple wells such that one or more organs attract fluids from one or more organs within a well plate aided by a microfluidic lid.

In accordance with yet another aspect of the present invention, there are provided methods fluidic transport across multiple wells in standard well format or custom well plate with simultaneous transport from/to one or more wells.

In accordance with yet another aspect of the present invention, there are provided methods to perform vascularization or anastomosis with endothelial cells and support cells in one layer while other cells including liver, lung, bone, muscle in another layer of transwell plate with membrane separating one or more layers.

In accordance with yet another aspect of the present invention, there are provided methods fluid deliver or removal from each well through one or more compartmentalized transwell membrane layers laterally or normally for multiple organs culture and interaction.

In accordance with yet another aspect of the present invention, there are provided methods to replace media or reagents from a standard well plate using pumps with multiple channels including peristaltic pump to deliver the reagents and to remove the reagents in parallel and sequentially.

In accordance with yet another aspect of the present invention, there are provided methods for media or reagents replacement using a single multichannel pump for delivery to the well plate and from the well plate while the media is continuously filtered using another pump.

In accordance with yet another aspect of the present invention, there are provided methods to use an intermediate container with multiple inlets and outlets to transfer fresh media and transfer to and from all the wells while the aforementioned container itself is filled with another pump and emptied with another pump.

In accordance with yet another aspect of the present invention, there are provided methods to directly transfer fresh media from a reservoir to standard well plate using multichannel pumps and to withdraw used or waste media from the wells to another container.

In accordance with yet another aspect of the present invention, there are provided methods to perform recirculation of media or reagents from standard well plate using multiple intermediate recirculation containers with one or more inlets and outlets which act as a buffer to transfer the reagents from well plates and to transfer back to the well plates.

In accordance with yet another aspect of the present invention, there are provided methods recirculation of reagents from well plate is enabled by two sets of multichannel pumps with the recirculation occurs within tubings of one of the pumps and perfusion occurs using above mentioned methods.

In accordance with yet another aspect of the present invention, there are provided methods for recirculation and perfusion on the same side of the well plate using the microfluidics lid accessing to transwell plates through fluidic tips.

In accordance with yet another aspect of the present invention, there are provided methods for connecting standard well plate to peristaltic pumps through microfluidic lid so that peristaltic pumps can open in the direction of the tubing or to the perpendicular direction of the tubing for rapid removal or exchange of the tubings.

In accordance with yet another aspect of the present invention, there are provided methods for concave ball bearings with flat circular surface and partial spherical surfaces.

In accordance with yet another aspect of the present invention, there are provided methods for performing peristaltic pumping using concave ball bearing rollers fitted to axial rods spinning in a ball bearing.

In accordance with yet another aspect of the present invention, there are provided methods for performing peristaltic pumping action for multiple channel using concave ball bearings to run on dual connected concentric paths.

In accordance with yet another aspect of the present invention, there are provided methods for recirculation using multiple pumps with concave ball bearing actuated by a single motor and connected linearly or circularly by gears.

In accordance with yet another aspect of the present invention, there are provided methods for perfusion using 3-d peristaltic pumps and recirculation using 2-d peristaltic pumps.

In accordance with yet another aspect of the present invention, there are provided methods for delivery of one or multiple reagents to a cell culture dish, mix multiple reagents and to remove the waste using air pressure or vacuum based pumping.

In accordance with yet another aspect of the present invention, there are provided methods for delivering fluids using gear pumps which can be rapidly mechanically attached or removed in the fluidic circuit for pumping.

In accordance with yet another aspect of the present invention, there are provided methods for the measurement of fluid liquid level for precise pumping using differential capacitance measurement with differential interdigitated electrodes.

In accordance with yet another aspect of the present invention, there are provided methods for the measurement of liquid level using outer electrodes with upright and inverted triangles.

In accordance with yet another aspect of the present invention, there are provided methods for improving the linearity and accuracy of liquid level measurements by cascading differential capacitance elements in parallel in one or more directions.

In accordance with yet another aspect of the present invention, there are provided methods for the measurement of liquid volume in microfluidic circuits for delivering liquids precisely using differential capacity measurements.

In accordance with yet another aspect of the present invention, there are provided methods differential measurements are measured using interdigitated electrodes with increasing lengths of side electrodes on one side and decreasing lengths of side electrodes on the other side.

In accordance with yet another aspect of the present invention, there are provided methods optical imaging integrated to fluidic delivery system to cells on culture.

In accordance with yet another aspect of the present invention, there are provided methods to integrate optical imaging and wirelessly transmitting the images to users or others.

In accordance with yet another aspect of the present invention, there are provided methods to acquire images of cells under culture and analyzing the cells for deprivation to control reagent constituents' delivery through machine vision and deep learning algorithms.

In accordance with yet another aspect of the present invention, there are provided methods to acquire audio signals from the pumps while operation and analyzing the intensity and frequency for flow of air and liquid in the pump to control the pumping.

In accordance with yet another aspect of the present invention, there are provided methods as a sequence of steps to perform media exchange in T-flask and the corresponding programming required in the electronics to accomplish media exchange in T-flask.

In accordance with yet another aspect of the present invention, there are provided methods to automate for the smart mass production of disposables connected fluidically by gluing the tubings using mechanical or laser drilling, dispensing glue and UV radiation through machine vision and deep learning.

Further aspects, elements and details of the present invention are described in the detailed description and examples set forth here below.

BRIEF DESCRIPTION OF THE DRAWINGS

The embodiments set forth in the drawings are illustrative and exemplary in nature and not intended to limit the subject mater designed by the claims. The following detailed description of the illustrative embodiments can be understood when read in conjunction with the following drawings, wherelike structure is indicated with like reference numerals in which:

FIG. 1A presents an exemplary diagram of a portable media exchange system in accordance with an implementation using T-flask for cell culture.

FIG. 1B presents an exemplary diagram of the portable media exchange system showing the battery compartment.

FIG. 2A presents an exemplary diagram of the disposables for the media exchange system.

FIG. 2B presents an exemplary diagram of the aliquots of reagents for injecting into the cells under culture.

FIG. 2C presents an exemplary diagram of the disposable pumping element.

FIG. 3 presents an exemplary diagram of a cGMP setup for cell culture with pumping media mixed with nanotherapeutic mixture.

FIG. 4A presents an exemplary diagram of pumping used media from T-flask to waste reservoir showing the directions of flow.

FIG. 4B presents an exemplary diagram of pumping fresh media from media container to T-flask showing the directions of flow.

FIG. 9A presents exemplary diagram of timing sequence for the pumps and valves for media exchange system.

FIG. 9B presents exemplary diagram of programming sequence for the stepper motor, pumps and valves for media exchange system.

FIG. 10A presents an exemplary diagram of user protocol and automation protocol for the cGMP media exchange system.

FIG. 10B presents an exemplary diagram of microcontroller programming sequence for the power saving electronic instrumentation.

FIG. 16 presents a series of protocols for the introduction of DNA plasmids through nanosomes in cells under continuous culture and to translate the RNA to proteins.

FIG. 17A presents a multiple reservoirs plugged in a lid for storing in cooler.

FIG. 17B presents the other side of the lid showing tubings and mechanical pumping elements to attach on pump array

FIG. 20A presents the diagram of closed chamber chips for electrical measurements and media exchange system.

FIG. 20B presents the diagram of closed chamber chips with port to deliver cells into the culture wells with electrodes.

FIG. 21 presents an exemplary diagram of the closed chamber chip with flow of media through vacuum and air pumps.

FIG. 22A presents an exemplary diagram showing closed chamber chip cell culture system with electrodes probes.

FIG. 22B presents an exemplary diagram showing closed chamber chip cell culture system with port to cell loading.

FIG. 23A presents a method to deliver reagents from a microfluidic plate to transwell system so that the media going to the cells are filtered by the membrane.

FIG. 23B presents a method to deliver reagents from a microfluidic plate to transwell system so that certain particulates in the media are retained within the cells culture chamber.

FIG. 23C presents a schematic to deliver fluids into transwell and to collect waste fluids from wells with transwell membrane separating channels.

FIG. 23D presents a top view of transwell membrane channel system for cells culture.

FIG. 28A presents a diagram of multiple compartment in layers of transwell insert where compartment in top layers are connected in parallel.

FIG. 28B presents a diagram of multiple compartment in layers of transwell insert where compartment in top layers are connected in series.

FIG. 28C presents a diagram of multiple compartment in layers of transwell insert in a standard well plate.

FIG. 29A presents an exemplary diagram showing multiple inserts in single well of standard well plate and microfluidic plate to transport fluidic across multiple inserts within well or across wells.

FIG. 29B presents an exemplary diagram showing side view of multiple inserts in single well of standard well plate and microfluidic plate to transport fluidic across multiple inserts within well or across wells.

FIG. 44 presents an exemplary diagram showing differential capacitance measurement configuration for precise pumping of fluidics.

FIG. 45A presents an exemplary diagram showing cascaded triangular electrodes for differential capacitance measurement.

FIG. 45B presents an exemplary diagram showing cascaded triangular electrodes where similar electrodes are connected through vias in printed circuits.

FIG. 45C presents an exemplary diagram showing the graph of volume or height of the liquid in a bottle as a measure of differential capacitance, while the bottle is filling and emptying.

DETAILED DESCRIPTION

Figure 5:
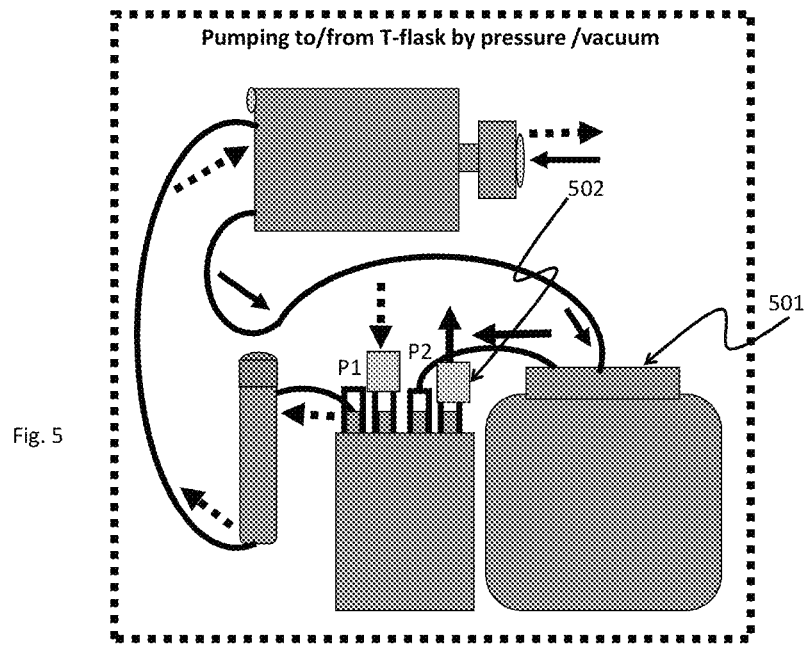
FIG. 5 presents an exemplary diagram of flow profile while pumping fresh media or used media to or from T-flask by pressure or vacuum respectively.

The following description contains specific information pertaining to implementations in the present application. The drawings in the present application and their accompanying detailed description are directed to merely exemplary implementations. Unless noted otherwise, like or corresponding elements among the figures may be indicated by like or corresponding reference numerals. Moreover, the drawings and illustrations in the present application are generally not to scale, and are not intended to correspond to actual relative dimensions.

This patent application deals with cell culture media or reagent addition, exchange or removal in T-flasks, multilayer flasks hyper flasks, cell bags, bioreactors, standard well plates, chips or dishes. Addition of multiple reagent containers for mixing the reagents before delivery into the cell culture container or addition of multiple reagents directly in the cell culture containers are also carried out. Moreover, storing reagents within an incubator for adding into the cell culture system is also carried out. The cell culture is extended to culturing organs or multiple organs system. Imaging the cells under built-in microscope and controlling the fluidics after feedback imaging and pumping schemes along with volume metering and control system are also addressed.

T-Flask Based System:

The system shown in FIG. 1A includes T-flask 101 connected to tube 102 with rubber cap 103 for injecting reagents in to cell culture and a waste bottle 104 to remove used reagents from cell culture. The system is portable and operates from batteries 105 as shown in FIG. 1B. The fluids are transported by pumping elements 106. It is easy to transport to microscope or incubator or tissue culture safety hood for current good manufacturing protocol in the workflow. The disposables are separated from the system and are packaged separately as in FIG. 2A. In order to inject certain reagents that will be stored in an fridge under cGMP procedure, syringe loaded aliquots (FIG. 2B) of the reagents are periodically brought to the system for injection. Care should be made to avoid any exposure or opening of the containers. The injection needles are wiped with disinfectant agent to avoid any contamination. The pumping element (FIG. 2C) includes electrical pins 201 to plug into the system by the users. The asymmetry in the pumping element helps the users to avoid problem from misconnection. FIG. 3 shows a special ingredient 301 such as nanosome mixture, reprogramming mixture to be added to media for continuous cell culture. The waste media is collected to a separate container 302. The mechanism of pumping of waste media from T-flask is shown in FIG. 4A While pumping, air 401 enters through the filters (size 0.2 um) in the T-flask and fill the vacuum generated due to pumping of waste media in to waste container. The waste container also has a filter (size 0.2 um) to release the air 402 inside the container. There could be a possibility to release the media from media reservoir into the T-flask. In order to avoid the unwanted flow the filter area is optimed and additional filter holes 403 are made in the T-flask. FIG. 4B shows the flow of fresh media in to the T-flask by another pumping element. The filter 404 in the tube helps the release of media into the T-flask. Therefore a closed container fluid operation essential for cGMP is achieved throughout the pumping.

Figure 6:
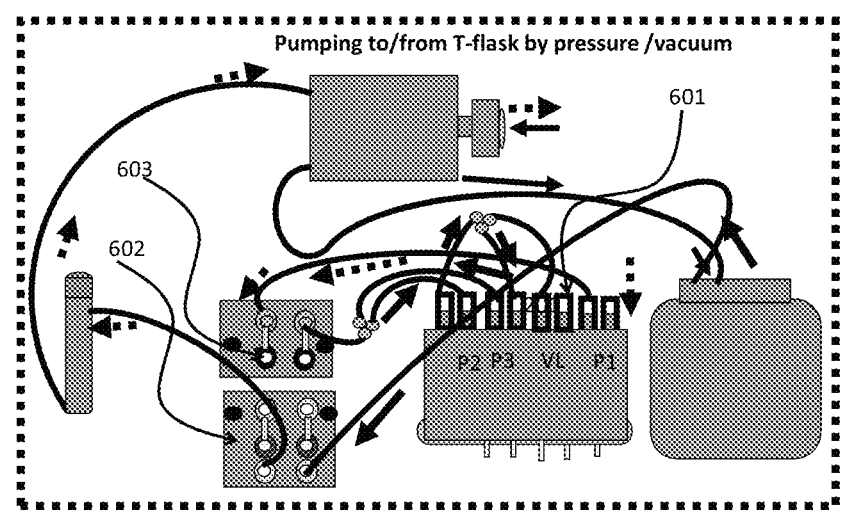
FIG. 6 presents an exemplary diagram of manifold with active pumping elements and disposable for media exchange system.
Figures 7A, 7B:
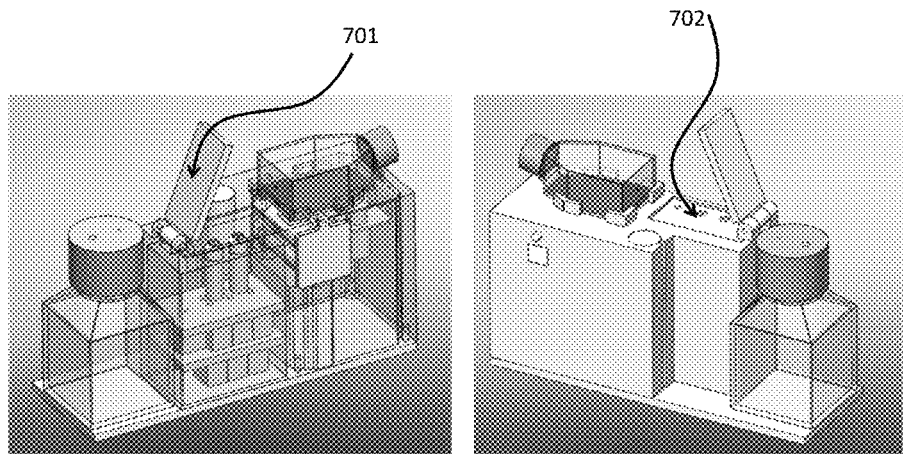
FIG. 7A presents and exemplary diagram of the cell culture system with hinge control manifold with O-rings for interfacing disposable.
FIG. 7B presents and exemplary diagram of another view of the cell culture system
Figure 8:
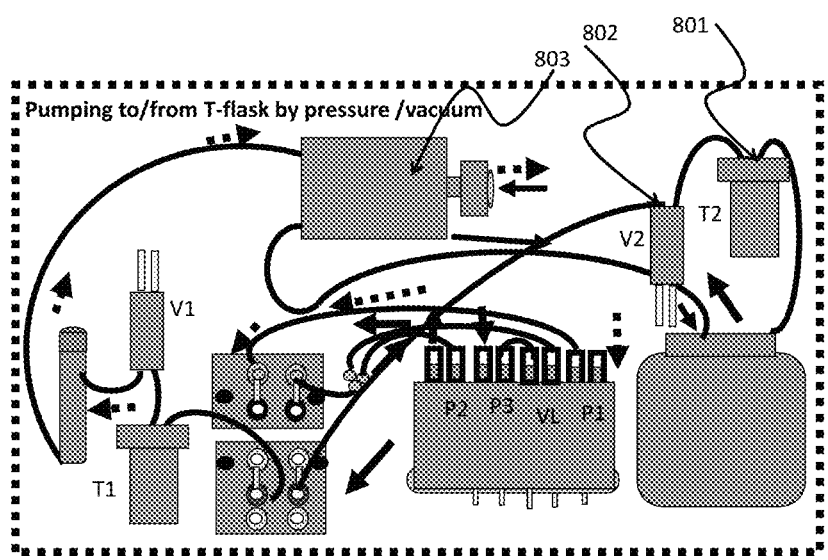
FIG. 8 presents an exemplary diagram of vacuum and pressure boost to the pumping system using additional tank and valve and programming.
Figure 11:
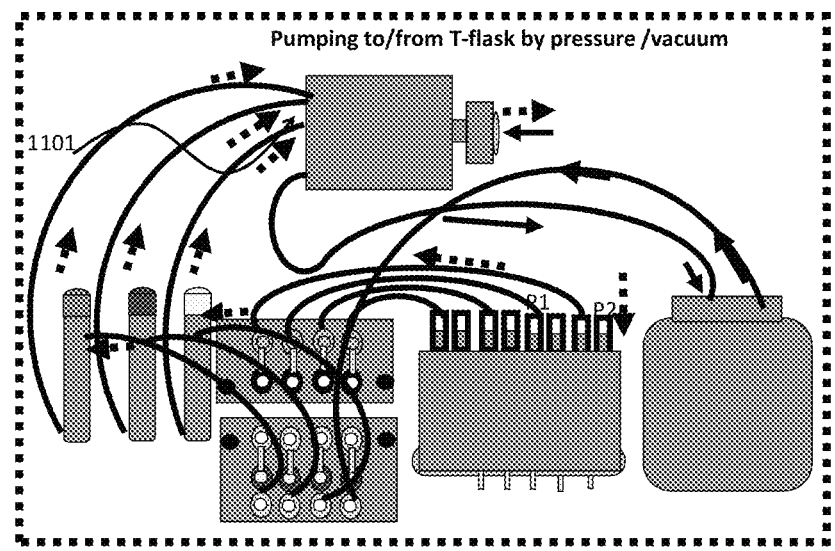
FIG. 11 presents a diagram of multiple reagents connection and pumping system for the cGMP cell culture system.
Figure 12:
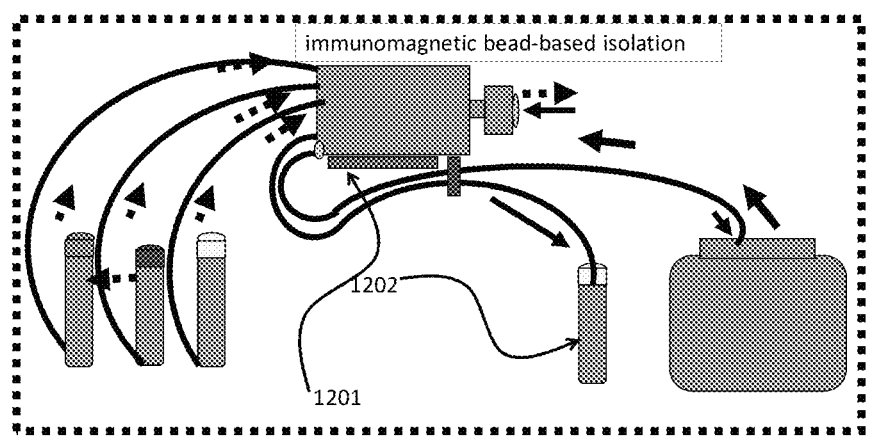
FIG. 12 presents a diagram to separate multiple components from the cell culture system using immunomagnetic bead based separation.

Isolated Pumping System:

In FIG. 5, vacuum is applied in to the waste container 501 from a vacuum pump through a filter 502 so that waste media from the T-flask will reach the waste container. For pumping the media from the tube a pressure is applied at the tube to release media in to the T-flask. In this system there could be a possibility of media going to the waste during the operation of fresh media pumping to the T-flask. Therefore a leak valve 601 and a positive pressure pumping is introduced in FIG. 6. The disposable elements interact with the non-disposable pumping elements using a chip 602 with O-rings 603. In FIG. 7A and FIG. 7B a 3-d model of the system is shown with manifold 701 and disposable chip connected to pumps and valves. The disposable fluidic exchange elements are connected to the cell culture media exchange system through a manifold with O-rings 702. The pumps and valves are kept in the non-disposable system. There is a possibility of bubbles in the tubings after every run and it will be difficult for the pump to clear the bubbles and air/water interfaces. In order to clear the bubbles, a boost vacuum or pressure is generated with the help of an extra tank 801 and a pump with a specified time of initial pumping that burst the bubbles to clear the tubings. FIG. 8 shows the extra tanks 801 and valves 802 to enhance the pumping to develop a robust cell culture system 803. In FIG. 9A timing diagrams of pumps and valves are shown. The vacuum pump P2 has two trains of pulses one for the vacuum boost 901 and the other for pumping media 902 out of the T-flask. The valve V2 is turned on to activate the flow with the pump P2. After the media is removed, valve VL is opened to vent the waste reservoir that will stop further pumping of the media from T-flask. The diffusion of air through valve VL may be slow and so pump P3 is activated in pulse so that venting can be faster. But the pump P3 activates in pulses 903 to avoid the generation of bubbles in the reservoir. The first media pump P1 is also activated along with valve V1 in two trains of pulses 904 to boost the pressure and release to clear the bubbles. The pulses of flow due to pump P1 also introduces pressure in the T-flask and any flow of media in to the reservoir is avoided by a proportion of pulses by pump P3. The flow sequence for the media exchange system is shown in FIG. 9B. The standard operating sequence of the user and machine are shown in FIG. 10A. Further electronics programming of instrumentation that will allow low power consumption is shown in FIG. 10B. Watchdog timer, long delay, deep sleep and stopping of the processor are implemented to allow low power operation so that the system can run for days to months from battery. Multiple reagents are added in cell culture system by separate pumping elements and are entered in to the cell culture independently through separate ports 1101 as shown in FIG. 11. Certain molecular species or particles during cell culture can be removed to separate contains through immunomagnetic separation by moving a magnet 1201 under the T-flask. After removing non-specific species, the specific species are removed by eluting the T-flask with a buffer and removing to a separate container 1202 as shown in FIG. 12. This system has application in ex vivo manufacturing which generally includes (1) immunomagnetic bead-based isolation of target cells, (2) cell supportive culture conditions with (3) defined gene modification reagents and conditions and finally, (4) removal of residual manufacturing reagents for preparation and testing of the final cellular product for infusion. All of these steps are carried out under cGMP, and the therapeutic genetic modification vary depending on the target patient population.

Figure 13A:
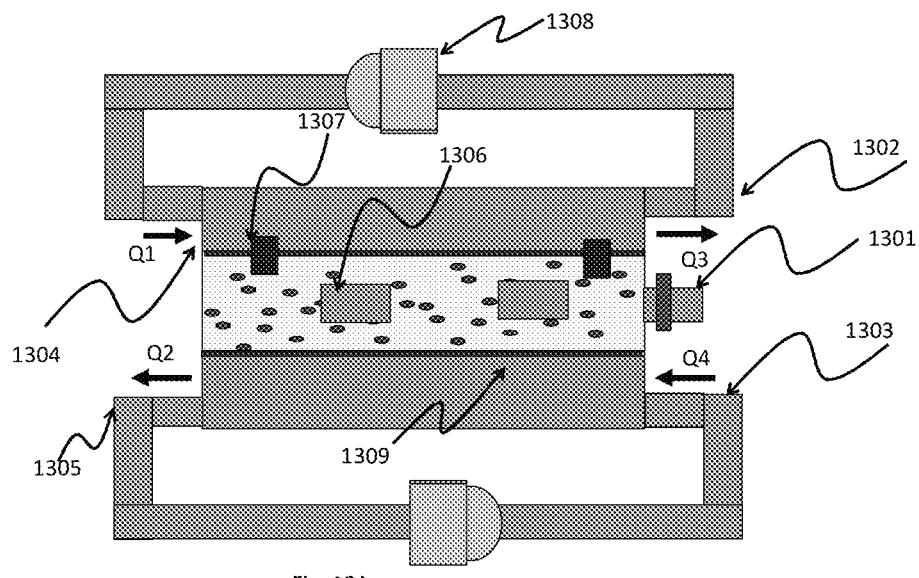
FIG. 13A shows cell culture in bags with media circulation where cells are within filters.
Figure 13B:
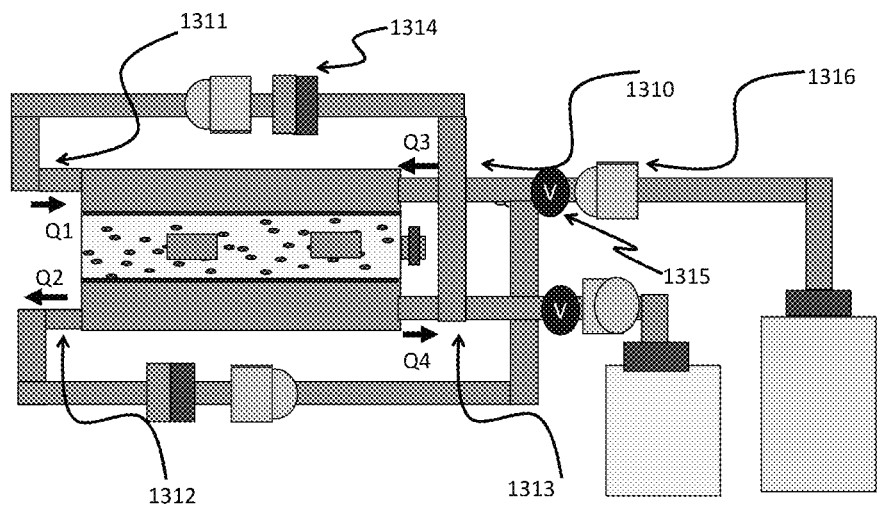
FIG. 13B presents a cell culture in bags where the flow is alternating between two outlets and periodically media is replenished.
Figure 14:
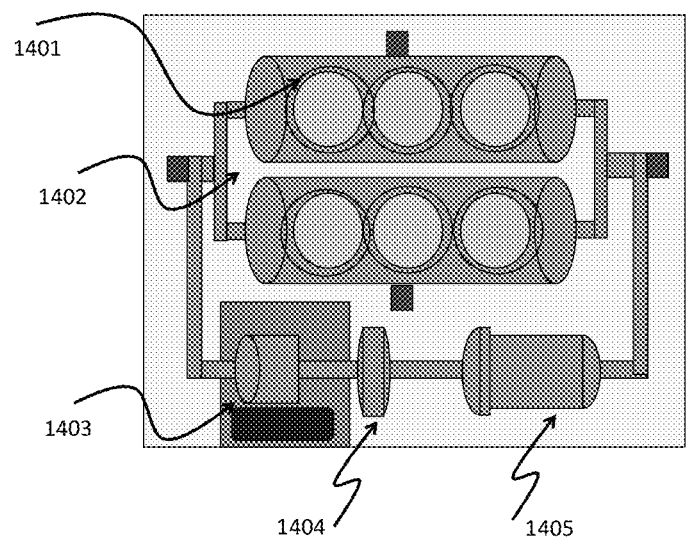
FIG. 14 presents an adherent cell culture system on filters or meshes with size of standard well plate wells.

Cell culture bags: Non-adherent cells are cultured in cell culture bags as shown in FIG. 13A with multiple inputs 1301, 1303, 1304 and outputs 1302, 1305. The cells are in cell compartment with has filters 1306 for oxygen/CO2 exchange, inlet outlet ports 1307 for instruments including pH probe, dissolved solids concentration and cell loading port. The outer compartments are for transporting the media and keep the cells under stirred condition through pumps 1308. The compartment is separated by filters 1309 size (eg 3 um, 5 um). In FIG. 13B, the inlets 1310, 1311 and outlets 1312, 1313 are connected alternatively so that better mixing is achieved. The cells are filtered 1314 throughput cell recirculation for any dead cells, toxins or other particles. The perfusion of fresh media are delivered in a periodic manner through valves 1315 by separate pumps 1316. Adherent cells are cultured in different compartments connected serially 1401 or parallelly 1402 or in combination of serial and parallel within cell bags. These cells are cultured in filters or meshes so that they can be moved to other cell culture vessels for further culture or performing additional assays. These compartmentalized cell culture bags are also used for transporting the cells to other laboratories or customers through continuous perfusion. The cells are loaded before closing the cell bags in compartments and the cell bags are glued by sterile pressure adhesive or sterile UV glue. Media is filled and bubbles are cleared through multiple ports. Pump 1403, filter 1404 and media reservoir 1405 are connected to the cell culture bags. The bag is placed on a tray substrate for packaged along with electronics and battery for perfusion control.

Figure 15:
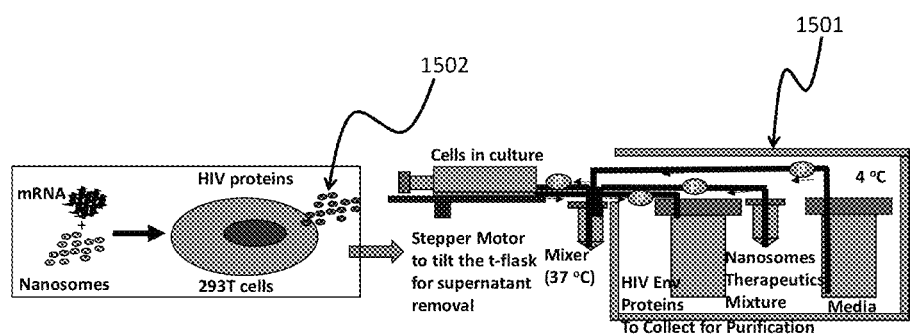
FIG. 15 presents a schematic of continuous cells culture with cGMP protocol for protein production from nanotherapeutic in cells where reagents are placed in the incubator at 4 deg C.

With Cooler to Store Reagents:

For continuous culture of cells and complete automation it is required to store the reagents for continuous cell culture in the incubator but at very low temperatures 1501 including 4 deg C. One of the applications is protein production under cGMP conditions systems particularly, HIV gp140 protein production 1502 shown in FIG. 15. Nanosomes containing respective self-amplifying mRNA (SAM) substrates are incubated with relevant producer cell lines (eg. CHO/293T cells) under standard culture conditions. To facilitate uptake, the cells will initially be treated with minimum standard medium containing the formulation, enough to cover the monolayer and allowed to rest for 2-4 hours before washing and adding growth medium. Thus treated cells will be cultured for 5-7 days, with media harvest and replenishment on days 3, 5 and 7. Harvested media are tested for HIV proteins using ELISA, pooled, concentrated and purified using affinity chromatography. A flow process for the cell culture cGMP process/bioreactor is shown in FIG. 16. After this initial validation, the proteins will be produced on quality assurance for product yield in multi-layer T-flasks, hyper flasks, cell bags and bioreactors under cGMP production.

Figure 18:
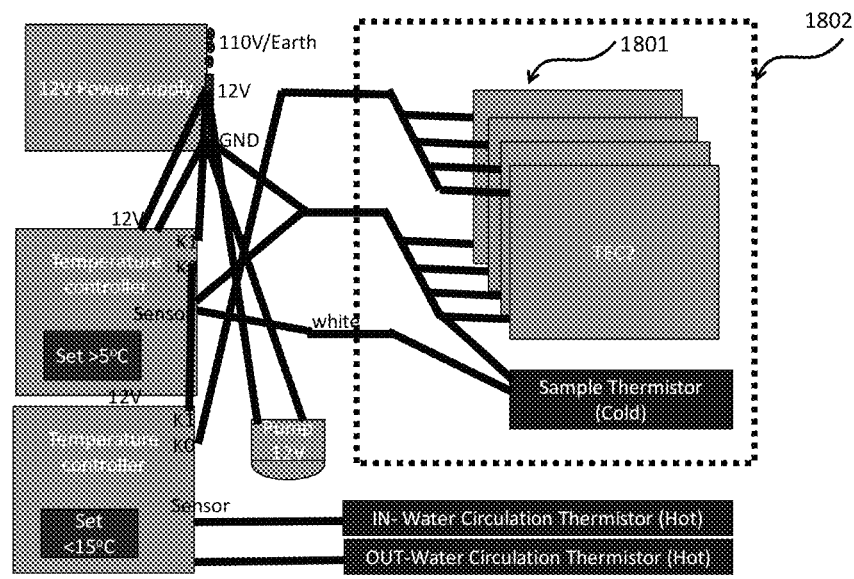
FIG. 18 presents an exemplary diagram of cooling system with thermoelectric coolers and control system.
Figure 19:
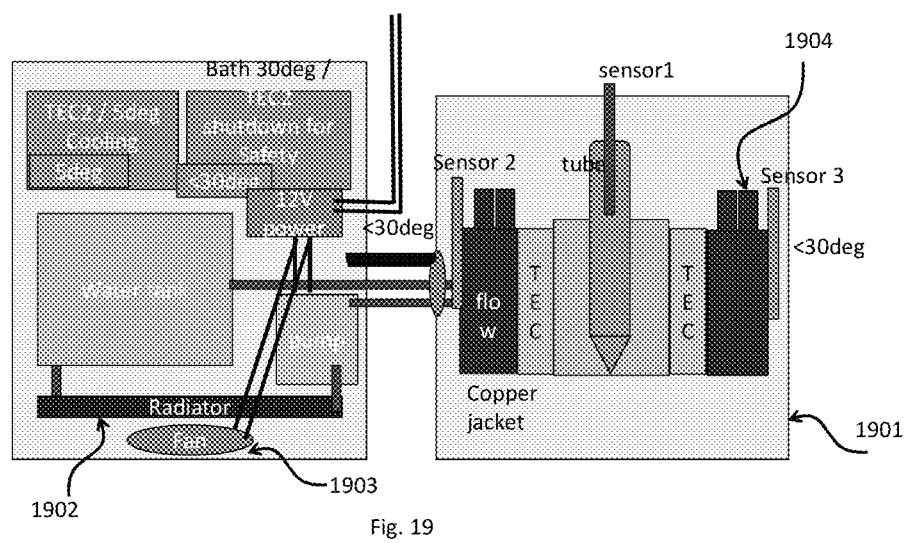
FIG. 19 presents an exemplary diagram of safe operation and cooling of thermoelectric coolers using water jacket and flow from a water tank.

In FIG. 17A a chip is designed with a 50 ml reservoir 1701 for media, a 5 ml reservoir 1702 for nanosomes storage, a mixing reservoir 1703 for 5 ml aliquot of cell media exchange and a 50 ml reservoirs 1704 for storing the supernatant from the cells. The caps 1705 of the reservoirs are integrated on the chip at the bottom. Fluidic portion of the pump array is attached to the chip. The chip is disposable and can be attached on the system and hold the T-flask where fluidic connections are drawn at the bottom-back (FIG. 17B). An electromechanical controller and a cooling system 1801 is developed as in FIG. 18. The controller hosts actuators for pumping, stepper motor for lifting the head of the T-flask and temperature control for 4° C. The thermoelectric cooling system is fixed at a corner of the incubator for storing media and therapeutic nanosomes. It takes around 30 minutes initially to bring the temperature down to 4° C. and the thermostat maintain the temperature. Thermal insulation 1802 is made between the incubator and the cooler walls. In FIG. 19 the cooling of the thermoelectric system is controlled with pumping the coolant liquid through copper water jackets 1901. The water is cooled at a radiator 1902 which is in turn cooled by a fan 1903. There are thermal sensors 1904 at the thermoelectric cooler elements to make sure they will not heat more than a set value for the safety of themselves.

Cell culture and assay on chips: Cells are cultured at the middle of the chip inside a channel 2001. The inlet 2002 and outlet 2003 of the chip is connected to fresh media and waste container respectively. A portable pumping system 2004 can keep the cells under perfusion and or recirculation. Optical imaging based assays are carried out in the chip with microscope. In a version of the chip shown in FIG. 20A, the chip is capable of having electrodes where cells can be grown and their field potential signals are measured with spring loaded connectors 2005. The cells are introduced through a hole 2006 in to the small well of the chip, on the electrodes through a pipette as shown in FIG. 20B. Height of the closed well is determined by the length of spring loaded connector. The cap 2007 of the cell introduction opening on the chip is closed. The chip is locked with spring loaded connector for field potential signal measurements. The fluidic controller is docked on the PCB for cycles of remove old media and add fresh media in to the cells. The operation of the chip is carried also carried out with vacuum and pressure pumping in to waste 2102 and fresh media 2101 container respectively under cGMP as shown in FIG. 21. The system can be portable and can be taken to a tissue culture hood for loading the cells as shown in FIG. 22A and can be stored in an incubator or microscope as shown in FIG. 22B under complete cGMP condition.

Figure 24A:
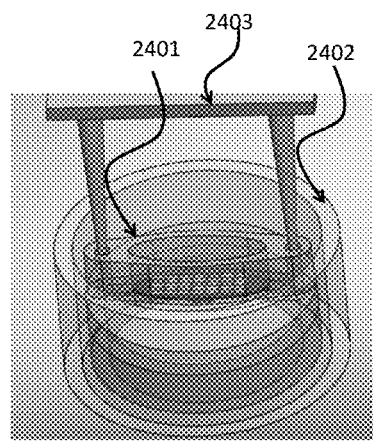
FIG. 24A presents an exemplary diagram of inlet and outlet wells for media delivery and withdrawal from transwell insert.
Figure 24B:
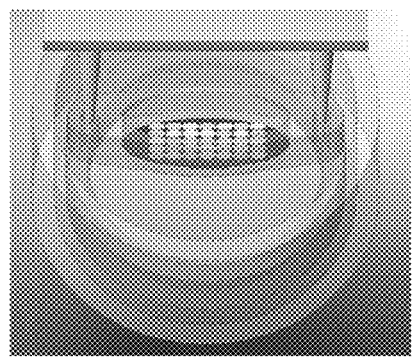
FIG. 24B presents an exemplary diagram showing cells within the transwell insert.
Figure 25:
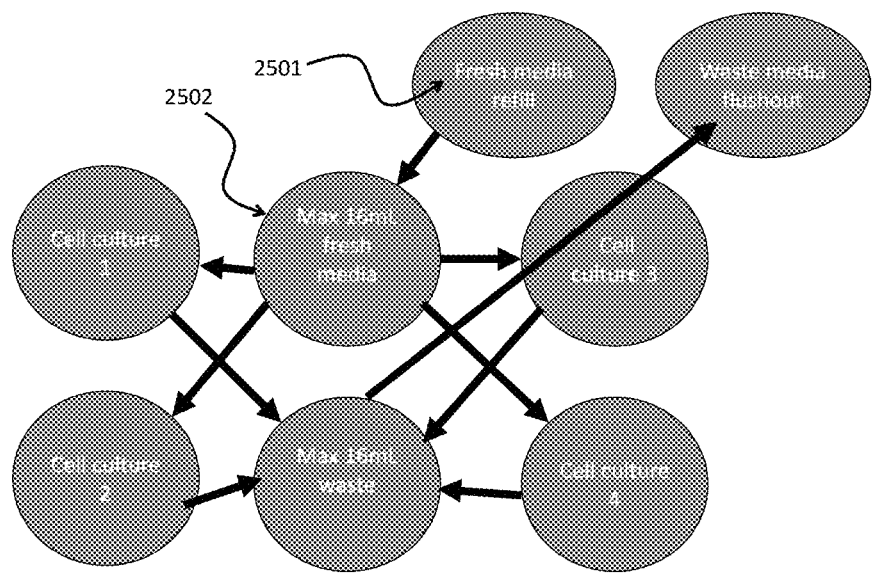
FIG. 25 presents an exemplary diagram of cell culture in 6-well plate with fresh media in a well and waste collected in another well.
Figures 26A, 26B:
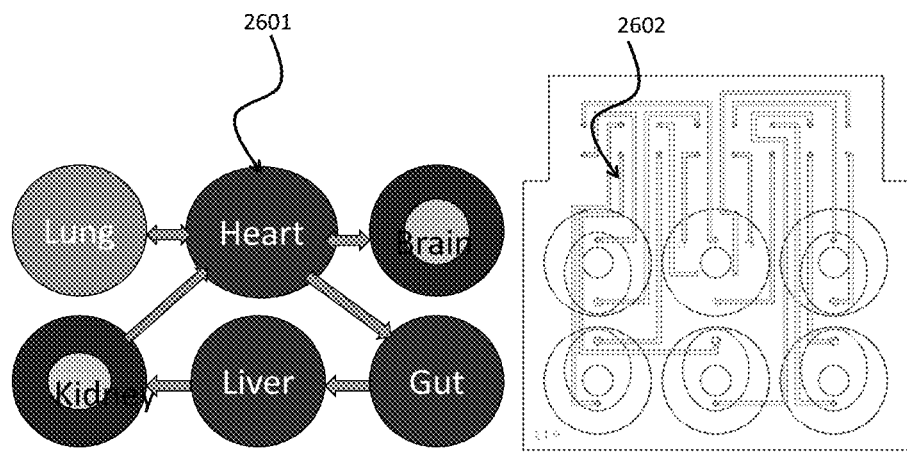
FIG. 26A presents a schematic of multiorgans culture.
FIG. 26B presents an exemplary diagram of channels in microfluidic plate for transporting fluids for multiple organs culture.
Figures 27A, 27B:
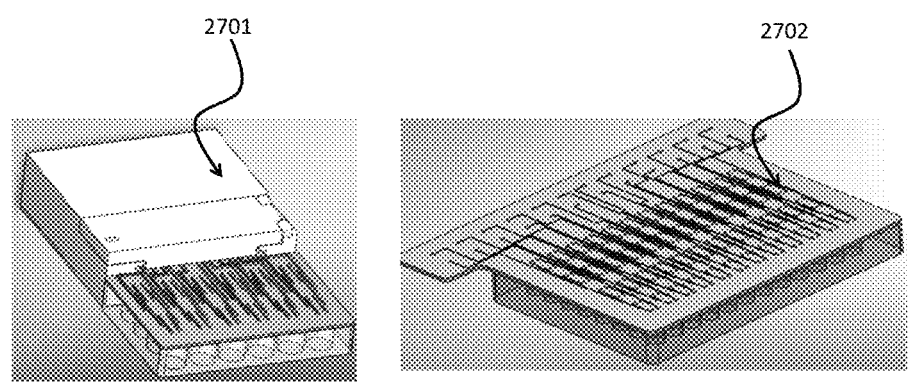
FIG. 27A presents an exemplary schematic diagram of parallel cell culture fluid delivery in multiple wells of wellplate.
FIG. 27B presents an exemplary schematic diagram of parallel cell culture fluidic delivery microfluidic plate showing fluidic inlet/outlet ports.

Cell Culture in Well Plates:

The cells cultured in well plates can be closed using a pressure tight material including silicon rubber 2301 and perfusion and recirculation of media to cells are carried out using microfluidic plates 2302. Cells can also be grown in inserts 2303 and the flow can be circulated from top to bottom as in FIG. 23A or bottom to top 2304 as in FIG. 23B through filter membranes. The insert can have inlet 2305 and outlet 2306 so that endothelial cells cultured can form vascular networks. Multiple cells along with endothelial cells can be cultured across channels in cell inserts as in FIG. 23C. Flow of media across the channel can be sustained constant by dropping the media at the inlet 2307 and pulling the media at the outlet 2308 using pumping system as in FIG. 23D. The 3-D insert 2401 that can hold multiple cells are introduced in wells 2402 and connected to outer microfluidic plate 2403 powered by the pumping system as shown in FIG. 24A and FIG. 24B. During cell culture perfusion, media can be stored within one or more of the wells and media can be refilled 2501. Similarly, waster media can be store in one or more of the wells and collected periodically. One of the wells in FIG. 25, is used for storing fresh media 2502 to supply four of the wells and another well is used for collecting used media from 4 of the well. The refresh rate of the media from outside bottle can be designed using original volume for cell culture (ml), media exchange volume (uL), period (hr) and first media exchange time (hr), if different. Multiple cells or organs can be cultured in different wells and circulation of media can be carried out from one or more wells to another well or more wells. In FIG. 26A heart organ 2601 is connected to four other organs and circulations of fluids are performed with four organs. The fluidic connections 2602 in a microfluidic plate for the above said circulations are shown in FIG. 26B. The system can be connected to pumping system 2701 to circulate or perfuse media in all the wells as in FIG. 27A. Multiple wells are connected together and can be tested for organs connections with drugs. Different concentrations of drugs are tested on different columns 2702 in the system shown in FIG. 27B. In a transwell plate insert with multiple layers different organs are cultured on a same layer 2801 in different compartments connected by microfluidic circuits 2802. Further different organs cab be made to interact with their related organs in another layer. In FIG. 28A, human vascular endothelial cells are cultured the top layer and multiple organs layers are cultured in the bottom layer. After assembling the layers in a well plate circulating tumor cells are flowed in the vascular endothelial network developed by the cells. Using this device cancer metastasis can be studied. In FIG. 28B, the vascular network channels are connected in series 2803 in the top layer to study metastasis of circulating tumor cells in liver, lung, bone and muscle cells. A well plate with multiple layers are shown in FIG. 28C. Multiple organs are developed in different layers 2901 of insert in each well as in FIG. 29A. The holes 2902 in the inserts helps to pull media from the bottom well as in FIG. 29B. The media dropped at the top layer enters to subsequent layers one by one through gravity while the pump system pulls the media from the bottom layer.

Figure 30:
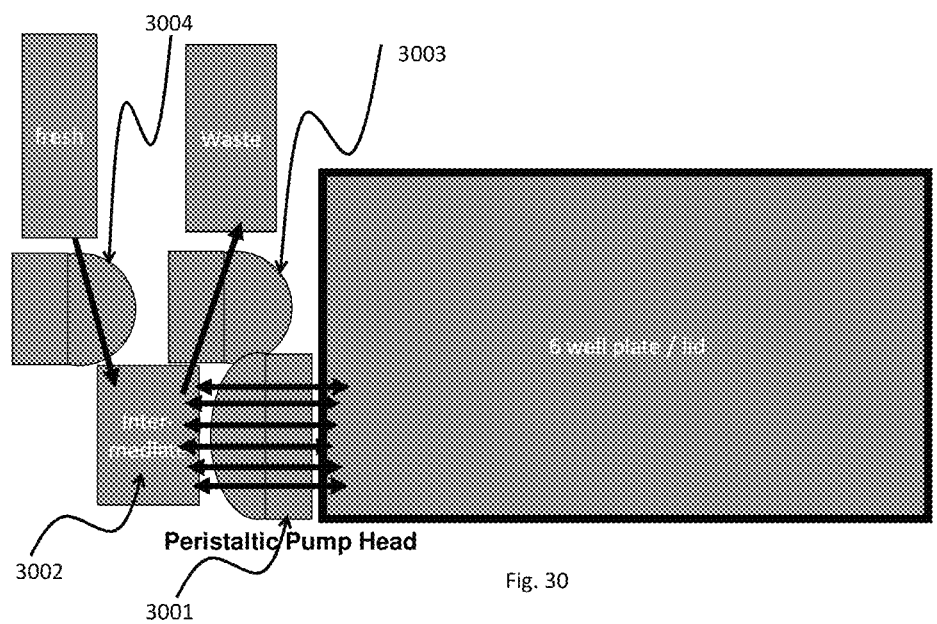
FIG. 30 presents a schematic of media replacement from standard well plate using an intermedia container.
Figure 31:
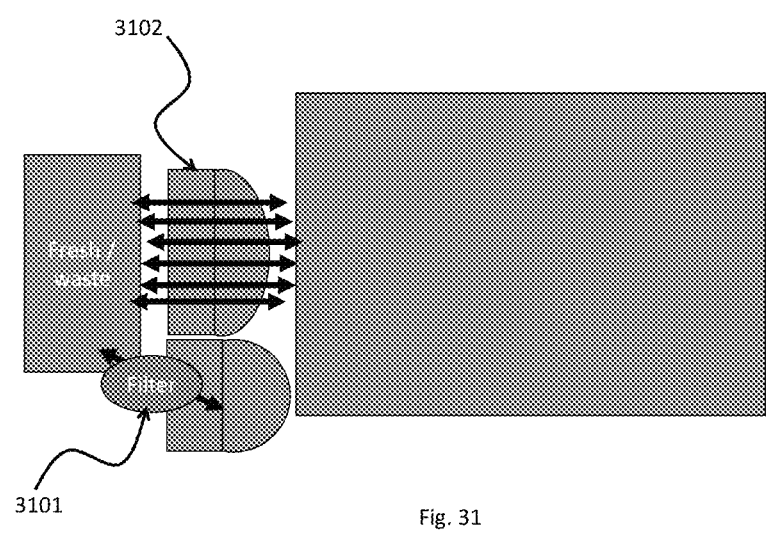
FIG. 31 presents a schematic of media replacement from standard well plate while the media is continuously filtered using another pump.
Figure 32:
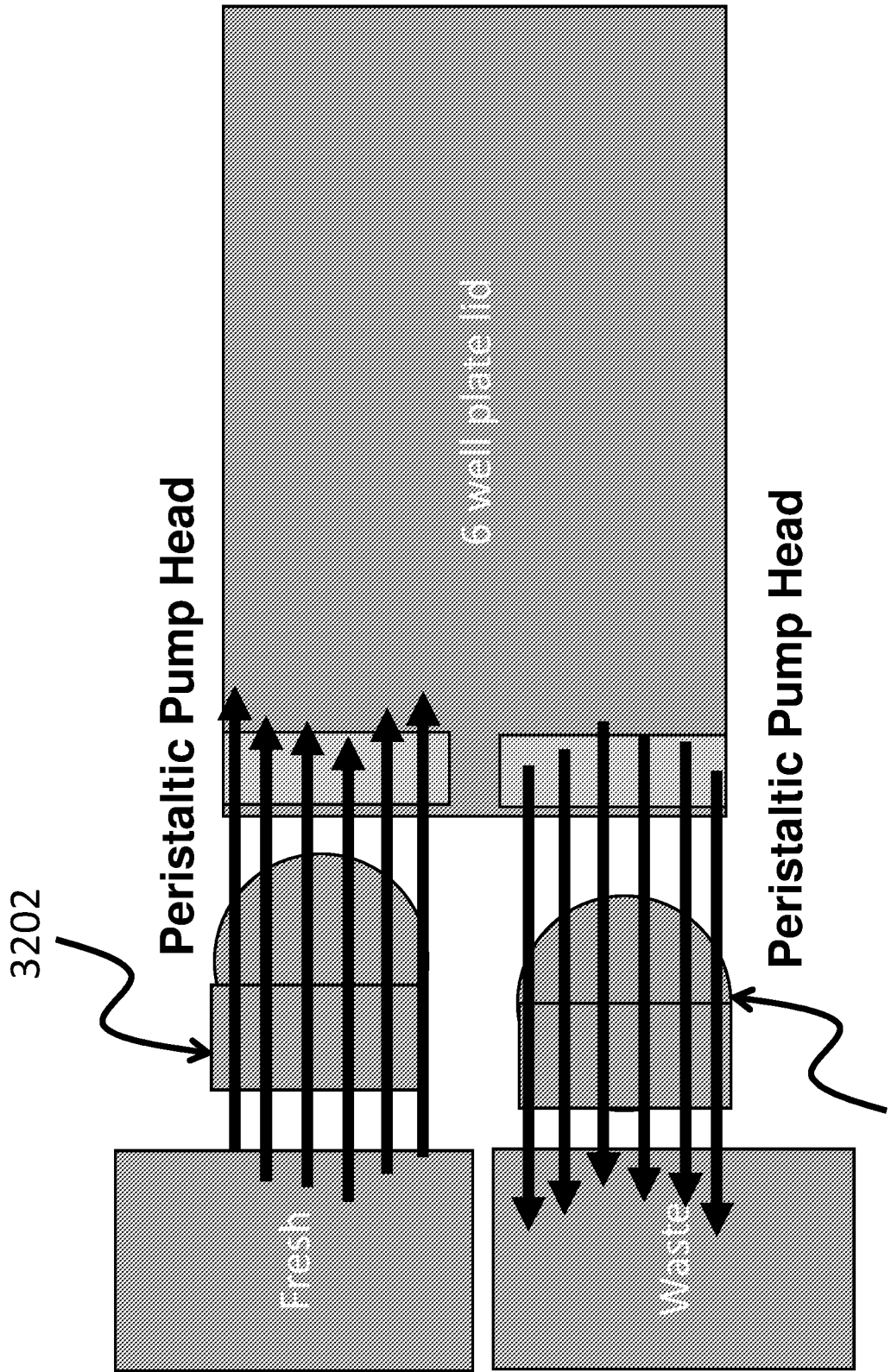
FIG. 32 presents an exemplary diagram showing direct media exchange from fresh media container and to waste container.
Figure 33:
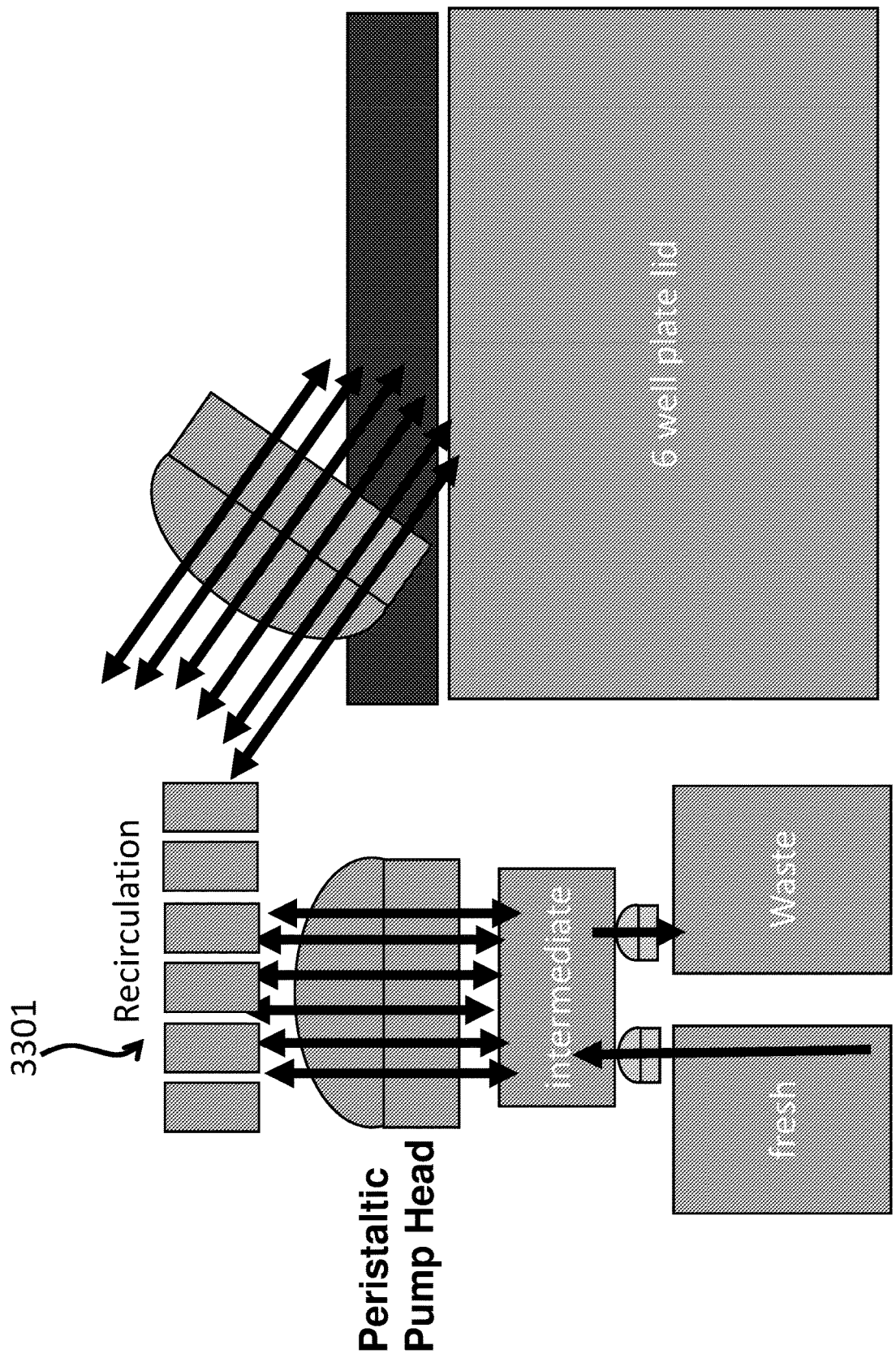
FIG. 33 presents an exemplary diagram showing recirculation and perfusion of fluids across multiple wells is accomplished by the use an intermediate container with multiple inlets and outlets
Figure 34:
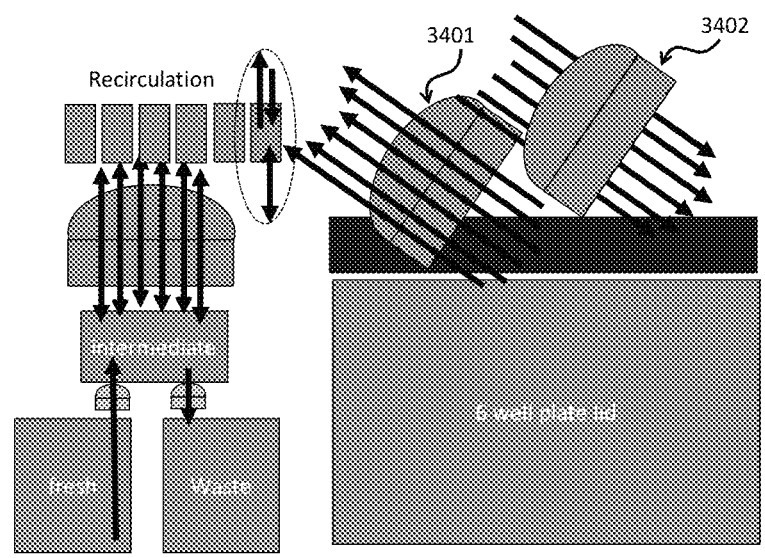
FIG. 34 presents an exemplary diagram showing recirculation and perfusion in a transwell plate insert.
Figure 35:
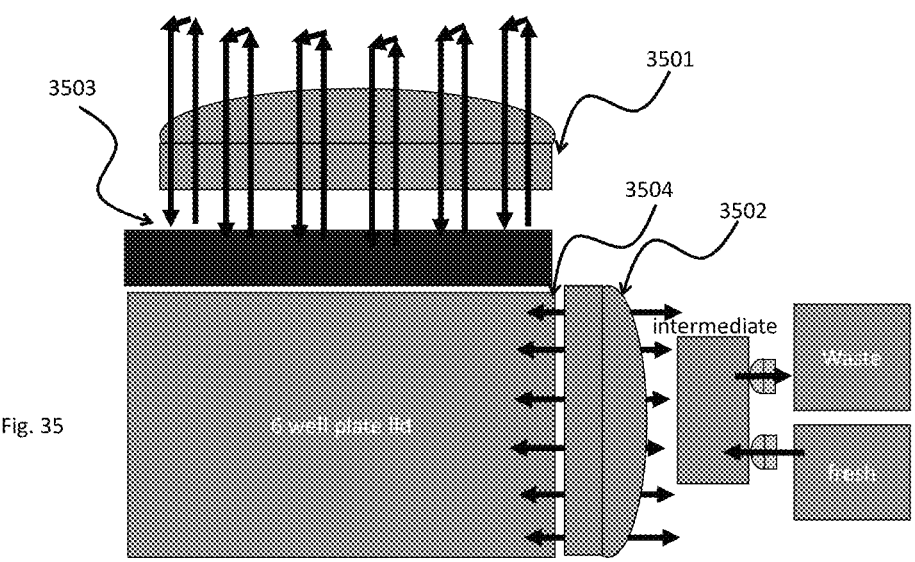
FIG. 35 presents an exemplary diagram showing recirculation and perfusion in a transwell plate insert using two sets of fluidic ports in a microfluidic plates.
Figure 36:
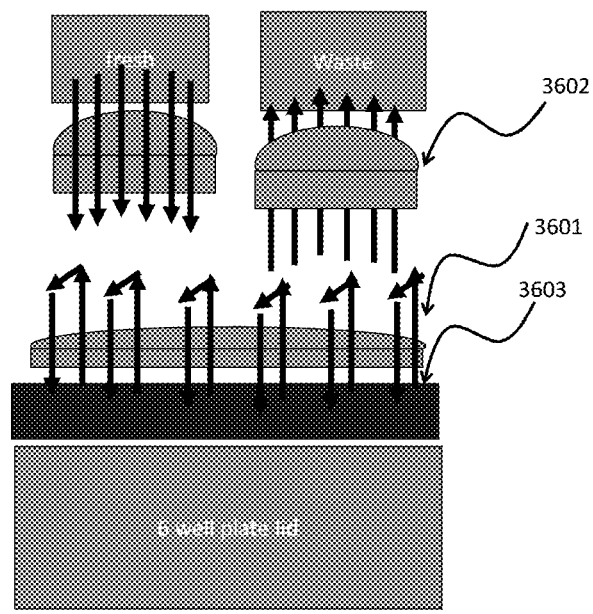
FIG. 36 presents an exemplary diagram showing recirculation and perfusion in a transwell plate insert using one or two sets of fluidic ports on the same side of microfluidic plate.

Perfusion and Recirculation in Well Plates:

It is important to remove the old media in cell culture on multi-well plates and replace with fresh media. There is also a requirement to recirculate the media across the cells to keep the cells refreshed with oxygen metabolism. Further it is required culture the cells in transwell plates with cell inserts. In all these cases replenishing the media and continuous recirculation of the media result in better proliferation, differentiation of cells. Media replacement in a 6-well plate is shown in FIG. 30. In this a multichannel peristaltic pump 3001 pumps the old media in to an intermediate container 3002 first then a single channel peristaltic pump 3003 transport the old media to waste container. Similarly, after the removal of the old medial, a single channel pump 3004 transports fresh media in to the intermediate container 3002 and let a multichannel pump 3001 to transport the fresh media to individual wells. In some cases the waste media can be refined by dialysis 3101 using a single channel peristaltic pump. Therefore only one multichannel pump 3102 continuous recirculate the fresh media in to each well as shown in FIG. 31. Further media replacement or media perfusion is carried out by independent multichannel pumps 3201, 3202 as in FIG. 32. First the media is removed by a pump 3201 from the wells and then fresh media is delivered into the wells by another pump 3202. Further recirculation of media from each well is performed by transporting to individual intermediate recirculation containers 3301 and transporting them back in to the designated wells as shown in FIG. 33. The recirculated media is refreshed by perfusion using previous methods. In order to recirculate media in to transwell inserts a separate multichannel pumps 3401, 3402 required since the media has to be pulled from one compartment and dropped in to another compartment as shown in FIG. 34. The media recirculation is separated from media perfusion by two set of separate pumps 3501, 3502 as shown in FIG. 35. In this a multichannel peristaltic pump for recirculation 3503 is connected at 12 ports of 6 well plate and the perfusion system 3504 is connected to separate 6 ports. Further, perfusion connections 3601 and recirculation connections 3602 can be shared the same ports 3603 for individual wells as shown in FIG. 36. The fluids to or from each well also shares the same fluidic channel on the microfluidic plates. In the case of microfluidic well with two layers of channels on the top and bottom of the plate, two set of 12 ports on the top and bottom with separate fluidic circuits are used.

Figures 37A, 37B:
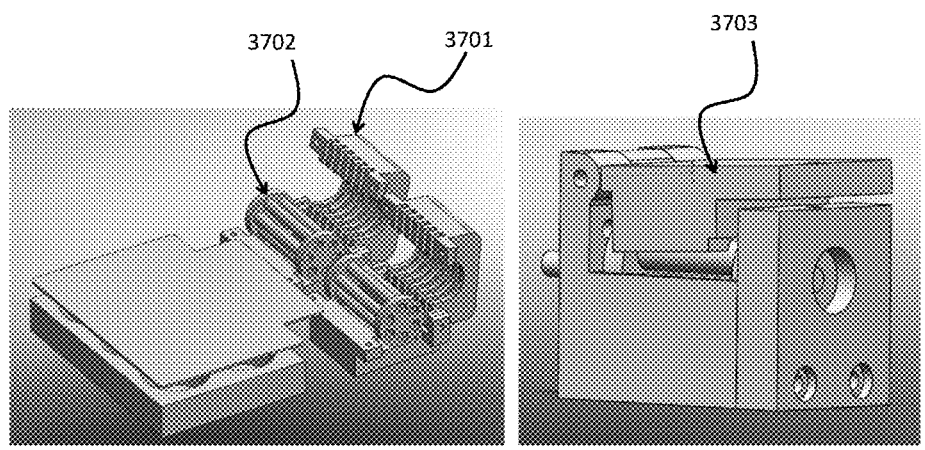
FIG. 37A presents an exemplary diagram showing peristaltic pump with multiple channels opening in the direction of the channels from microfluidic ports.
FIG. 37B presents an exemplary diagram showing peristaltic pump with multiple channels opening in the direction perpendicular to the channels from microfluidic ports.
Figure 38A:
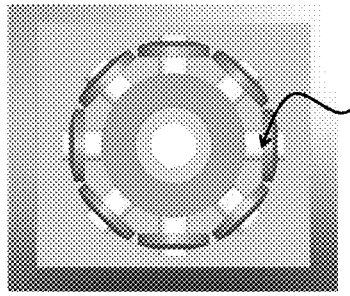
FIG. 38A presents an exemplary diagram showing top view of surface peristaltic pump concave rollers attached to ball bearings of axial rods of spinner.
Figure 38B:
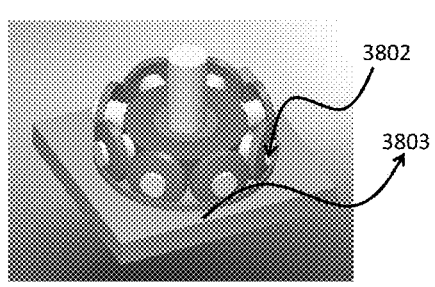
FIG. 38B presents an exemplary diagram showing tubing and channel for the pumping using the concave roller peristaltic pump.
Figure 38C:
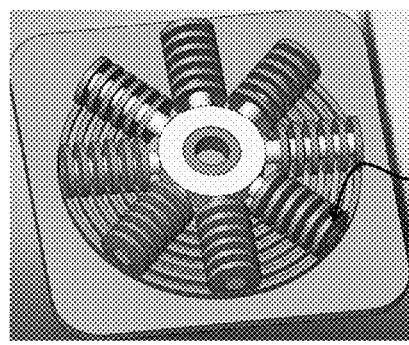
FIG. 38C presents an exemplary diagram showing multiple channels peristaltic pump with multiple concave rollers with ball bearings.
Figure 39:
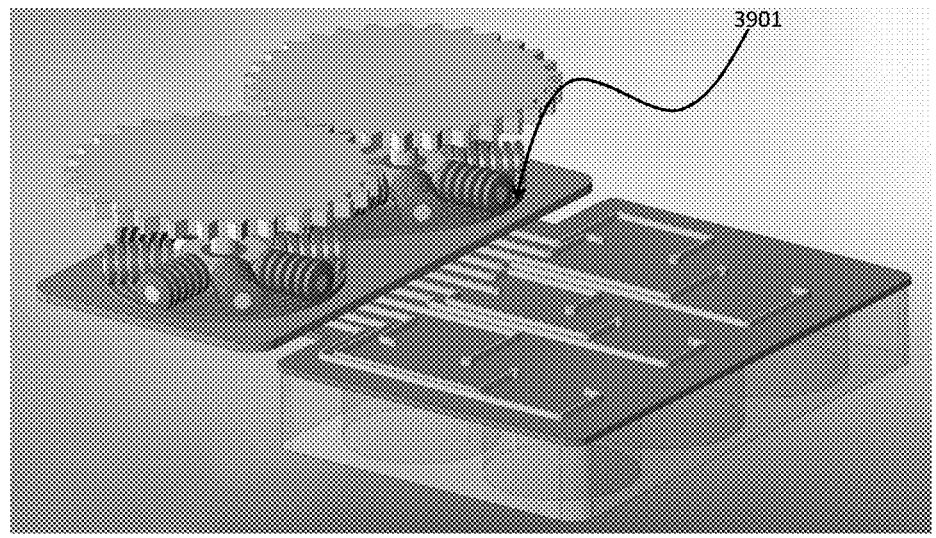
FIG. 39 presents an exemplary diagram showing surface peristaltic pump with multiple channels in connected pair of 'S' circular channels or tubings.
Figure 40:
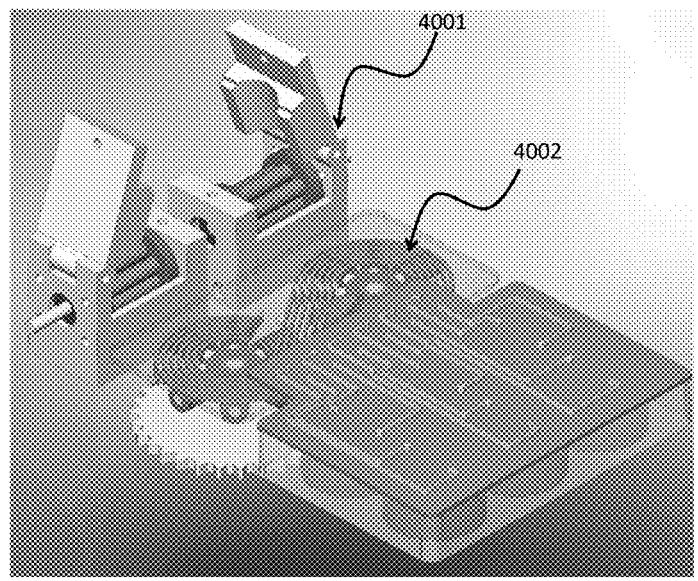
FIG. 40 presents an exemplary diagram showing perfusion and recirculation using multiple peristaltic pumps.
Figure 41A:
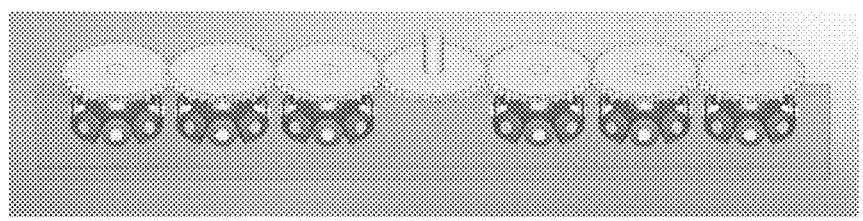
FIG. 41A presents an exemplary diagram showing surface peristaltic pump with multiple pumping arranged in a linear format actuated by a single geared motor.
Figure 41B:
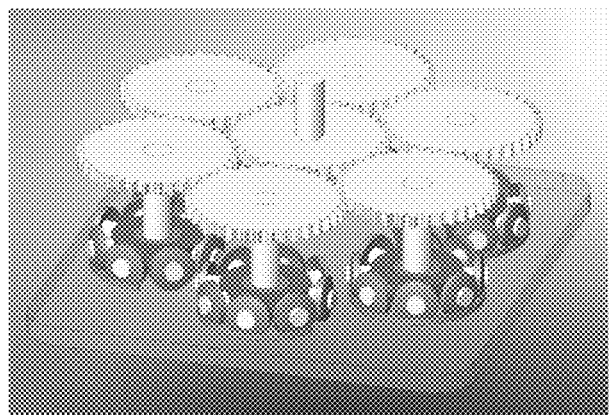
FIG. 41B presents an exemplary diagram showing surface peristaltic pump with multiple pumping arranged in a circular or hexagonal format actuated by a single geared motor.
Figures 42A, 42B:
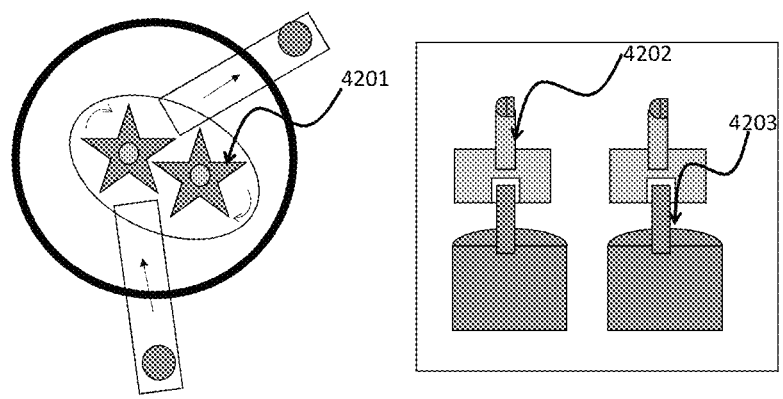
FIG. 42A presents an exemplary diagram showing a gear pump for delivering fluids.
FIG. 42B presents an exemplary diagram showing rapid attachment or detachment of gear pump for users of media exchange system.
Figure 43:
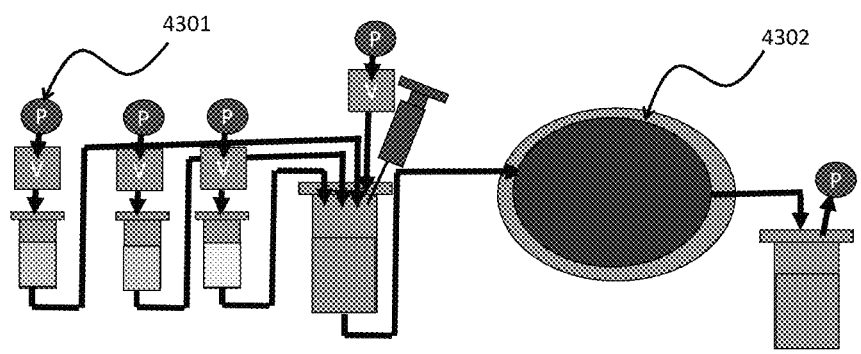
FIG. 43 presents an exemplary diagram showing multiple reagents delivered to a cell culture dish.

Pumping and monitoring A multichannel peristaltic pump 3701 for driving 6-channel perfusion for 6-well plates is shown in FIG. 37A. In this pump the tubings are connected to around the roller 3702 and it is difficult to remove the tubings rapidly. In the peristaltic pump shown in FIG. 37B, the tubings can be removed rapidly by lifting the lid 3703 of the pump and removing the tubings sidewards. The peristaltic pump pushes a tubing inserted in a channel 3801 to develop the pumping action as shown in FIG. 38A. In this surface peristaltic pump, the rollers are made to a sphere segments 3802 with ball bearings inserted in the middle, are connected radially to the spinner. The sphere segment is concave inside and convex outside so that it will smoothly travel in a channel where tubing is buried. The tubing also can be replaced by microfluidic channel 3803 covered by soft layer. The key is to make the rollers travel in a perfect circular path. If it were just cydrical rollers, the edges of the cylindrical rollers will cause friction at the circular channels during the circular motion. Therefore spherical segment rollers are required for efficient pumping. In FIG. 38B the tubing and channel 3803 for the pumping using the concave roller peristaltic pump is shown. Multichannel surface peristaltic pumps (shown in FIG. 38C) are created with multiple rollers 3804 along the radial direction of the spinners. Each radial roller circulate in each circular channels where tubes are buried and stuck to the bottom. Two set of multichannel surface peristaltic activators are connected together to press two circular channels connected as 'S' channels 3901 as shown in FIG. 39. Perfusion 4001 and recirculation 4002 can be accomplished using two set of 3-d peristaltic pumps and a 'S' shaped surface peristaltic pump as shown in FIG. 40. Six set of peristaltic pumps are created in a linear path (FIG. 41A) or in a circular/hexagonal path (FIG. 41B) and are activated by a geared motor. To pump fluidics gear pump (shown in FIG. 42A) with plastic gears 4201 in a channel pumps the fluid and provides higher pressure. Such gear motor is connected in parallel for multichannel pumping as in FIG. 42B. In order to isolate fluids with the metal axis, a plastic slotted adapter 4202 is connected to the metal axis 4203. Multiple pumps are connected to multiple containers with different fluids to deliver different reagents to cell culture dish 4302 as in FIG. 43.

Figure 46A:
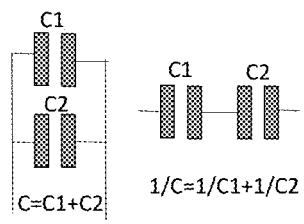
FIG. 46A presents an exemplary diagram showing basic capacitance additions in series and parallel for capacitance measurement.
Figure 46B:
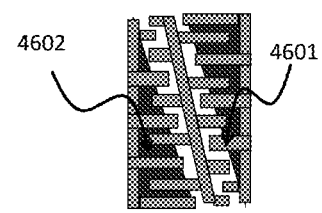
FIG. 46B presents an exemplary diagram showing differential interdigitated electrodes forming upright and inverted triangles.
Figure 46C:
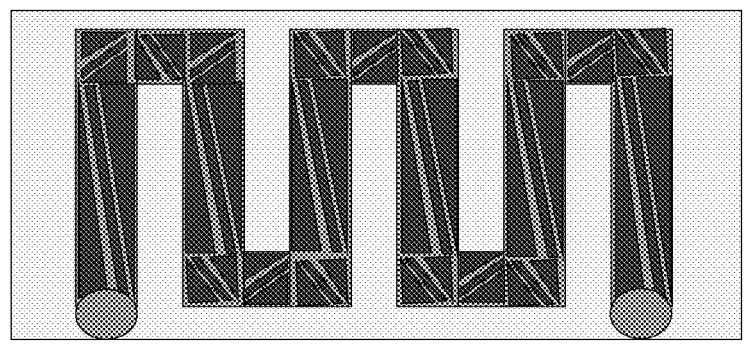
FIG. 46C presents an exemplary diagram showing differential electrodes circuitry in channels for fluid volume measurements.

In order to accurately pump fluids in to cell culture, there need to be a feedback system to monitor the fluid level. Capacitance based volume metering of fluid is implemented with capacitance measurement using the electrodes shown in FIG. 44. The electrodes configuration based on interdigitated triple electrodes. The dual capacitance from both sides of the electrodes gives the proportional measure of the volume or height of the fluid level. Further differential capacitance measurement using upright right-triangle 4501 and inverted right-triangle 4502 with the middle electrodes 4503 gives a measure of water level or volume of water. Cascading of multiple differential capacitances as in FIG. 45A gives a linear relationship between capacitance and height/volume of water column. Similar electrodes are connected together through vias 4504 in printed circuit in the horizontal direction in order to increase the sensitivity and linearity. Cascading 4505 in the vertical direction (as shown in 45B) and arithmetic operations on the capacitances can provide improvement in the capacitance and thereby volume/height measurement. In FIG. 45C presents the graph of volume or height of the liquid in a bottle as a measure of differential capacitance, while the bottle is filling and emptying is shown. The arithmetic operations are in accordance with the measurement of series and parallel equivalent capacitances as shown in FIG. 46A. Interdigitated differential electrodes are formed with decreasing length 4601 of the side electrodes on one side and increasing length 4602 of the side electrodes on the other side as shown in FIG. 46B. The interdigitated electrodes are implemented in the volume measurement for very sensitive and linear volume metering. Further, differential electrodes are integrated in microfluidic channels as in FIG. 46C as series and parallel and capacitance measurement is continuously measured with the volume of fluid dispensed out of the microfluidic channel. The fluid is released at the outlet and pressure is set at the inlet to dispense fluid. Accurate dispensing is achieved by feedback differential capacitance measurement.

Figure 47A:
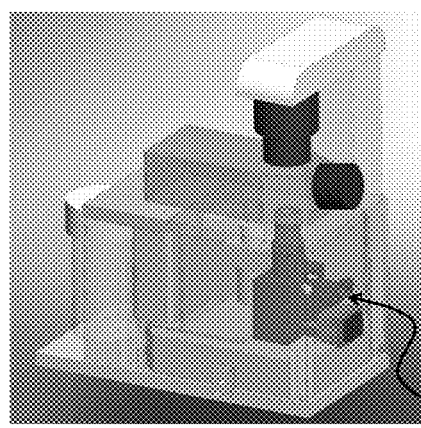
FIG. 47A presents an exemplary diagram showing microscopic imaging using cell culture.
Figure 47B:
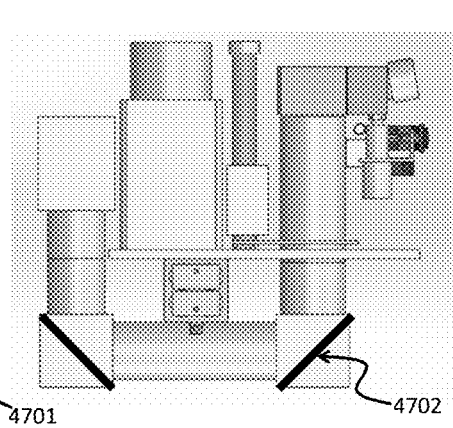
FIG. 47B presents an exemplary diagram showing another view of microscopic imaging using cell culture.
Figure 48:
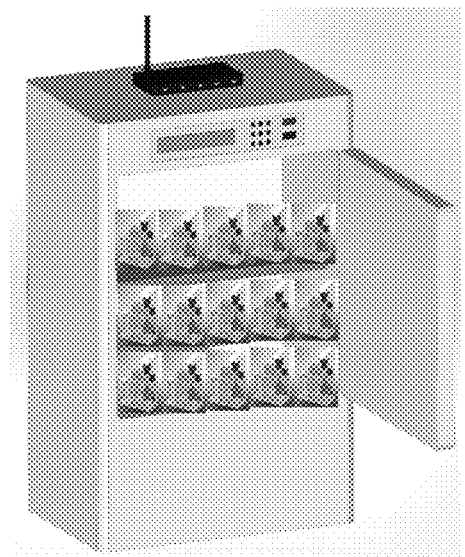
FIG. 48 presents an exemplary diagram showing multiple media exchange system stored in an incubator.
Figure 49A:
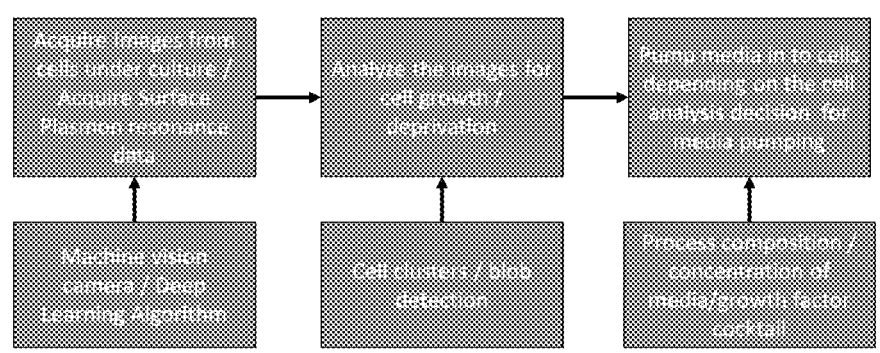
FIG. 49A presents an exemplary diagram showing media exchange through machine vision control.
Figure 49B:
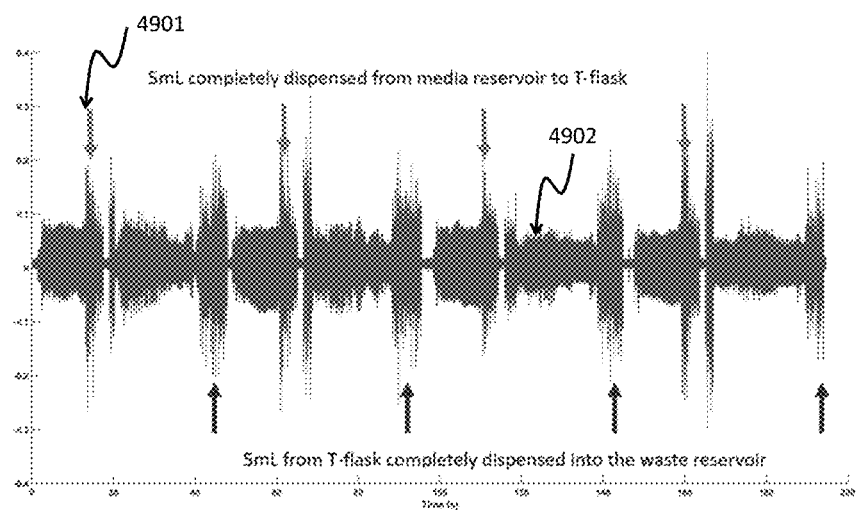
FIG. 49B presents an exemplary diagram of intensity of audio signals from the pumps while operation showing water completely dispense from T-flask and reservoir.

Further cell culture media exchange system is integrated with microscopic imaging 4701 as shown in FIG. 47A. The system is compactly made with two slanted mirrors 4702, objective, eye-piece and camera with electronic control circuits for blue-tooth or wifi communication shown in FIG. 47B. The system can send periodic images of cells or cell clusters to users. Many such cell culture and monitoring systems can be accommodated in an incubator and the cells are monitored remotely as shown in FIG. 48. The imaging of the cells and cell clusters can also provide the state of the cells for perfusion control as described in FIG. 49A. The images of the cells are acquired and machine vision is applied on the cells with deep learning algorithms. The cells are analyzed for growth or deprivation nutrients. The concentration, composition or media with growth factors or other factors can be made with multiple pumps and released to the cells for better differentiation or molecular and cellular phenomena in the cells. In 49B, audio signals from the pumps during operation are analysed for detecting flow of air 4901 and liquid 4902 in the pump to control the pumping. This helps in stopping the pump as soon as the liquid withdrawal or pumping is completed. Further SPR sensors integrated to the system is for measuring binding evening from the analytes in the media provides additional information to the cell secretion, excretion and cellular processes to control the media exchange system.

Figure 50:
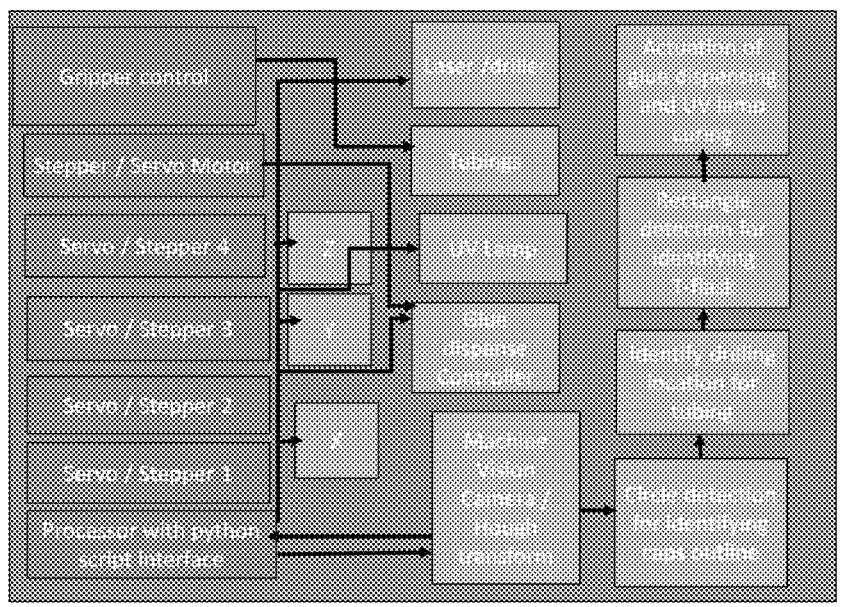
FIG. 50 presents an exemplary diagram showing the system for the manufacturing of disposable for media exchange system.

Manufacturing:

Manufacturing of the disposables are carried out by machine vision and actuation. The machine vision system with multiple axes is cable of drilling the caps, T-flasks, vials and locating the position for gluing and curing with UV lamp. Tubings are inserted using grippers. The processes with python script interface can compute Hough transform for images in real time. Hough transforms are computed for the detection of circles for caps, vials and bottles and detection of rectangles for T-flask. FIG. 50 shows the manufacturing techniques using machine vision control.

EXAMPLES

1 Closed Culture System for Efficient and Reproducible Differentiation of Human Pluripotent Stem Cells into Islet Cells Human stem cells have attracted as cell sources to regenerative medicine and drug screening due to their self-renewal capabilities and pluripotency. Various types of somatic functional cells can be obtained by differentiating stem cells in vitro by mimicking the process of embryonic development. There are clinical trials in progress for the treatment of several diseases such as age-related macular degeneration, Parkinson's disease, spinal cord injuries, myocardial infarction, and type I diabetes. With the present cell culture system, it has been difficult to reproduce published results, even when the reported procedures were strictly followed. These discrepancies may be caused by differences in cell strains or culture media, or inexperience with regard to cell culture techniques. These discrepancies are true for stem cell differentiation. Differentiation of human induced pluripotent stem cells to pancreatic endocrine cells are prepared in an agarose-gel microwell plate and maintained in series of culture media containing different factors and chemicals. The differentiation efficiency is both technician and lot dependent and it is difficult to maintain sterile conditions in the microplate over the 30-day culture period due to the frequent replacement of culture media. Therefore, a closed culture system to reduce the risks to differentiate into pancreatic islet cells is important for efficiency and reproducibility. The issues regard to achieving reproducible differentiation of cells with the required functionality for realizing human transplantation therapies and with regard to reducing the potential for bacterial or fungal contamination, can be solved using the closed culture system.

The scalability of the culture system is important for regenerative medicine, as a huge number of cells will be required to realize human transplantation. Some automatic robot systems that can handle increased numbers of culture dishes but they are expensive and bulky. However, a low-cost, simplified closed-channel system with microwell structure will be suitable for making quality-managed functional islet cells. Medium replacement in this culture system could be achieved by microfluidic pumping and its closed structure make it easy to maintain aseptic condition.

2 Culturing Human Pluripotent and Neural Stem Cells in an Enclosed Cell Culture System for Basic and Preclinical Research Standard stem cell culture techniques suffer from several environmental constraints that place undue stresses on the cells and expose the cells to unacceptable risks of contamination. Among the stresses that cells may endure under present cell culture conditions are precipitous changes in the levels of carbon dioxide and oxygen concentrations. This occurs when the cells are moved from the incubator to the biosafety cabinet and/or microscope which may not be optimal for the cells. The risks of cellular contamination are higher as the laboratory environment and personnel impinge upon the cells at almost every step of their culture and manipulation. Traditional clean rooms comprise one effective method to greatly decrease contamination risks but they are expensive, have a large footprint and fail to address stressors related to carbon dioxide and oxygen concentrations. A cell production facility that can address both contamination risks and gas concentrations and that can be qualified to meet cGMP criteria provides high quality cells for basic science research as well as clinical applications. Using the closed cell culture system, a wide variety of tasks can be performed, such as standard feeding of pluripotent stem cells and multipotent neural stem cells, as well as Sendai virus-based reprogramming and differentiation of neural stem cells.

3 Automated Closed-System Expansion of Pluripotent Stem Cell Aggregates in a Perfusion Bioreactor A need for large-scale pluripotent stem cell culture is emerging for applications in pluripotent stem cell banking, the commercial production of cells, and cell expansion for clinical trials. Feeder-free pluripotent stem cell culture and suspension aggregate culture have enabled large-scale cell expansion in flasks and bioreactors. The advantages of suspension culture avoids some of the challenges that occur when culturing pluripotent cells on traditional microcarriers, including the inefficient seeding and release of cells from carriers, the physical separation of microcarriers and cells during harvest, and cell carrier clumping that changes the phenotype of the cells. Moreover, suspension aggregates are more biologically similar after directed differentiation and maturation than cells grown in 2D culture. Control of aggregate size may also influence the efficiency of directed differentiation and maturation.

Presently, pluripotent stem cell expansion and differentiation on microcarriers suspension aggregate culture in bioreactor system has been carried out by an open centrifugation step for passaging cells. However, the ideal solution for cGMP culture is closed-system manipulation at each step of the process (including seed, perfusion, passage, and harvest), which allows for the maintenance of sterility in closed systems, reduces costs, and reduces human intervention so that any potential contamination is avoided. The perfusion platform by flow of media in the culture fluid, providing continual mixing and aeration, resulting in a robust, lower-shear environment for cell growth. The single-use disposable bioreactors require no cleaning or sterilization, providing ease of operation and protection against cross-contamination. Provision are made to perform continuous or discontinuous perfusion or medium exchange in a closed system, with monitoring of dissolved oxygen, CO2 levels and pH, temperature, weight, pump speeds and gas exchange, with real-time controls and data storage.

The closed platform bioreactor enables closed system and hands-off expansion of pluripotent stem cell aggregates. Automated processes for medium exchange via software-controlled perfusion, gas exchange, and maintaining other key process parameters in conjunction with the ability to passage within the bioreactor enable a fully closed workflow that could benefit cGMP pluripotent stem cell production for both commercial and clinical processes. A major benefit to performing all steps in a closed manner is the reduced likelihood of user-induced contamination due to manual processing. Automated medium exchange and closed-system passaging methods avoid any open steps that could introduce a contaminant, ensuring that the cell product remains sterile.

4 Large-Scale Clinical Expansion of Mesenchymal Stem Cells in the GMP-Compliant, Closed Automated Cell Expansion System Mesenchymal stem cells (MSC) production with GMP compliance to maintain the quality and safety of MSCs provides the best condition to use MSCs in clinical application. The researchers for MSC transplantation have focused on degenerative and immune system related diseases. The clinical grade MSCs are only produced by application of regulations as well as the requirements or elements of GMP. Several clinical protocols in different settings including hematopoietic cells or solid organ transplantation, and severe or refractory autoimmune disorders require large number of ex-vivo expanded cells in a GMP-compliant, functionally closed, and automated bioreactor system. In the platforms for ex vivo culture of MSCs using monolayer and suspension culture, the MSCs only grow in an adherent state. In monolayer culture, MSCs are plated in flasks or dishes with a treated surface while in suspension culture, MSCs adhere to microbeads suspended in media.

5 Automated Closed System Manufacturing of Lentivirus Gene-Modified Haematopoietic Stem Cells for Gene Therapy Haematopoietic stem cell (HSC) gene therapy has demonstrated potential to treat many diseases. However, current state of the art requires sophisticated ex vivo gene transfer in a dedicated Good Manufacturing Practices facility, limiting availability. An automated process would improve the availability and standardized manufacture of HSC gene therapy. Automated cell isolation and culture equipment to permit complete benchtop generation of gene-modified CD34 þ blood cell products for transplantation. These cell products meet current manufacturing quality standards for both mobilized leukapheresis and bone marrow, and reconstitute human haematopoiesis in immunocompromised mice. Importantly, nonhuman primate autologous gene-modified CD34 þ cell products are capable of stable, polyclonal multilineage reconstitution with follow-up of more than 1 year. Given the many target diseases for gene therapy, there is enormous potential for this approach to treat patients on a global scale. However large global health burdens such as HIV and hemoglobinopathies, lack of a portable technology for standardized manufacture of gene-modified CD34 þ blood cell products which becomes a critical barrier to widespread clinical use. Presently, the protocols for ex vivo lentivirus vector (LV)-mediated gene transfer into CD34 þ haematopoietic cells and targeted gene editing for retrovirus genomic insertion introduces the risk of contamination with infectious agents and reduces engraftment potential and haematopoietic fitness. Thus, a short ex vivo manipulation protocol in a closed system would represent a significant advance in the field, permitting distribution beyond a small number of sophisticated centers. Our closed system, automated manufacturing platform with minimal user interface could accomplish all of the steps in the ex vivo manufacture of genetically modified CD34 þ cells suitable for human infusion and haematopoietic repopulation, while meeting cGMP criteria.

6 an Integrated Miniature Bioprocessing for Personalized Human Induced Pluripotent Stem Cell Expansion and Differentiation into Neural Stem Cells With the current Human induced pluripotent stem cell culture technologies and bioprocessing, the cost for biomanufacturing clinical-grade patient specific iPSCs and their derivatives are very high and not affordable for majority of patients. Therefore, the advancement of iPSC-based personalized cell therapies is currently hindered by the high cost to biomanufacture the cells. The use of closed and miniature cell culture device for biomanufacturing patient specific neural stem cells (NSCs) from iPSCs can assist iPSC expansion, iPSC differentiation into NSCs and the subsequent depletion of undifferentiated iPSCs from the NSCs. With reprogramming factors, adult cells from the patient, such as fibroblasts, can be reprogrammed into iPSCs within about one month. iPSCs can be cultured for long term and expanded into large numbers under complete defined conditions. They can be differentiated into presumably all the cell types of the human body. The protocols for efficiently differentiating iPSCs into various human cell types, such as cortical neurons gamma-aminobutyric acid (GABA)-ergic interneurons, midbrain dopaminergic (DA) neurons, endothelial cells, mesenchymal stem cells, cardiomyocytes, hepatocytes, beta cells and other cells have been developed. Many of these cells are being investigated for treating degenerative diseases and injuries, such as Parkinson's disease (PD), Alzheimer's disease (AD), stroke, spinal cord injury (SCI), blindness, myocardial infarction (MI), diabetes etc. With the current bioprocessing, patient cells are collected and cultured for a few days; then, reprogramming factors are delivered to these cells to reprogram them into iPSCs (which takes approximately one month). Next, high quality iPSC clones are selected, expanded and characterized for their pluripotency and genome integrity with a variety of assays (which takes approximately one to two months); then, iPSCs are expanded and differentiated into the desired cells. Finally, the produced cells are purified, characterized for their identities, purity, and potency and formulated for transplantation. The whole bioprocessing takes a few months and is mainly done using 2D cell culture flasks through manual operations—a processing which leads to low reproducibility, high risk of contamination, and requirement for highly skilled technicians. The whole bioprocessing is also required to comply with the current Good Manufacturing Practice (cGMP). Maintaining these plates requires large incubator and cGMP-compliant facility space, labor, and reagent. If large numbers of patients need iPSC-based personalized cell therapies, the cell production can only be done in large cell biomanufacturing centers (i.e. the centralized cellular biomanufacturing). Patient cells are sent to the center, and the produced cells are sent back to the point-of-care for transplantation. This centralized biomanufacturing has additional disadvantages, including: (i) patient cells may be cross-contaminated and (ii) there are high costs and risks associated with the transportation, logistics, tracking, and recording.

One method to significantly reduce the biomanufacturing cost is to make cells in individualized, closed, computer controlled miniature cell culture device at the point-of-care (i.e. the cGMP-in-a-box production). Using closed culture devices avoids contamination risk and eliminates the requirement for cGMP processing. Automation of all key operations avoids output variations and reduces need for highly skilled operators. Biomanufacturing at the point-of-care reduces the cost and risk related to the logistics and transportation. Miniaturizing the culture system makes it possible to simultaneously biomanufacture cells for large numbers of patients at the point-of-care (i.e. high throughput biomanufacturing). Using this bioprocessing, human iPSCs could be expanded in 3-d thermoreversible Poly(N-isopropylacrylamide)-Poly(ethylene glycol) (PNIPAAm-PEG) hydrogels at high growth rate and yield. In this paper, we first developed a protocol that could efficiently differentiate human iPSCs into NSCs in the PNIPAAm-PEG hydrogel. We then, with the assist of this hydrogel scaffold, integrated the bioprocessing including the iPSC expansion, iPSC differentiation into NSCs, the subsequent depletion of undifferentiated iPSCs from the product, and concentrating and transporting the produced cells to the surgery room into two closed, 15 ml conical tubes.

7 Efficient, Scalable and Stable cGMP Antigen Production Environment for HIV Env Proteins RNA-based therapeutics hold great promise in the progress towards alternative HIV therapies. To these ends, nucleic acid vaccines including messenger RNA (mRNA), circular DNAs that encode mRNAs, plasmids, splice-switching oligonucleotides, antisense oligonucleotides, minicircles, are variously being studied to advance therapeutic innovations for a wide range of diseases. Indeed, self-amplifying mRNA vaccines (SAM), have in various studies when coupled with nonviral delivery, produced potent and robust innate and adaptive immune responses in small animals and nonhuman primates. In these trials, SAMs of positive-strand RNA viruses delivered in nanoemulsions were able to induce in situ, potent cellular immune responses orders of magnitude greater than SAM vaccine delivered by traditional viral vectors. RNA delivery strategies that ensure RNA stability and potency and coupling these delivery strategies with RNA-based immunogen expression with large-scale production of proteins for clinical trial needs is supported by recent vector strategies in which constitutively secretion functional HIV gp140 trimers could be scaled up for the production of env immunogens. In order to test and optimize a manufacturing scale for high quality HIV Env immunogen, envelope production in CHO cell lines are coupled by combining the use of a synthetic self-amplifying mRNA (SAM) of prototype HIV, with nanoemulsions to produce gram-range quantities of envelop in a non-vectored delivery system.

Closed systems for mass production under cGMP guidelines, are important because regulatory authorities' license biological entities along with how entity is produced, tested, and released for use. HIV vaccines protocols are currently not sufficiently optimized at producing large quantities of vaccine needed for clinical evaluation. Evaluation looks at vaccine route, dose, formulation, and efficacy. Issues with vaccine production consist of the lack of high yield antigen reproducibility, and variability in antigen product. There are a number of purification methods used to remove contaminants from end product, but these do not mitigate for the inevitable low yield. Advances in vaccine technology look to create higher viral titer, lower cross-contamination risks, cut-down experiment time, real-time monitoring, and ease isolation of end product. Bioreactors enable reduced production costs and optimization of both yield and quality. For example, a fed-batch perfusion system can achieve higher cell concentration causing increased viral yield. Disposable bioreactors bridge the manufacturing optimization pathway for vaccines; they cut down on experimental set up time, isolation of product, and potential cross-contamination risks. HIV like many enveloped viruses that are target of novel vaccine development are more stable when cultivated using adherent cells. These adherent cells have been demonstrated to also to grow optimally in vaccine culture production as microcarriers, cell-stacks, and packed bed bioreactors. A systematic process to develop HIV envelop proteins in bioreactor system reduces variability for each step of vaccine production and maximizes yield.

The invention claimed is:

1. A method for closed cell or organ culture system, the method comprising:
- connecting at least one or a plurality of containers through fluidic channels or tubings;
- tilting the cell culture system to move one or a plurality of fluids towards one or a plurality of outlets;
- performing, optional removal of old media partially or fully;
- adding fresh media, drug or reagents into cells in culture from one or a plurality of containers;
- displacement of gas or air in and out of the cell culture system from one or a plurality of containers through filters to avoid any contaminants into the cell culture system; and
- restoring the tilt of the cell culture system for incubation.

2. The method of claim 1, wherein one or a plurality of disposable systems are plugged to play in non-disposable system through one or a plurality of methods involving electrical, mechanical and fluidic contacts for one or plurality of processes comprising activation, sensing and monitoring.

3. The method of claim 1, wherein aliquots of drug or reagents are delivered into the cells in culture through closed elastic caps by piercing them and still maintaining closed state.

4. The method of claim 1, wherein pre-processing or post-processing of cells in a closed container using multiple reagents through immunomagnetic beads by applying magnetic field from permanent magnets or electromagnets.

5. The method of claim 1, wherein the culture of suspension cells or cell aggregates in compartments separated by filters is performed using fluidics.

6. The method of claim 1, wherein positive train of flow pulses are used for moving the fluids from one container or a plurality of containers to another container or a plurality of containers whereas negative train of flow pulses are used to avoid any back flow in one or a plurality of coupled fluidic systems.

7. The method of claim 6, wherein periodic or aperiodic pumping of air across a container or a plurality of containers with or without monitoring their internal pressures, to keep the pressure balanced for any backflow or contamination from one or a plurality of containers.

8. The method of claim 6, wherein clearance of bubbles in one or plurality fluidic loops are achieved by boosting the pressure or vacuum and restoring the flow of reagents using a set of one or a plurality of pumps and valves.

9. The method of claim 6, wherein coupled fluidic loops are optimized for avoiding any backflow using timings of air/vacuum fluidic pulse sequences.

10. The method of claim 1, wherein methods for collecting selected one or plurality of species cells, proteins and other analytes from cells in culture from a closed container through immunomagnetic magnetic beads by applying magnetic field.

11. The method of claim 1, wherein one or a plurality of reagents for cell culture are stored in refrigerated containers at low temperature while the entire system is in incubator.

12. The method of claim 1, wherein one or a plurality of multistep cell based molecular assays involving transformation, amplification purification, encapsulation, introduction, fusion and translation are performed in closed system.

13. The method of claim 1, wherein cells are delivered in closed chamber chips through a side inlet and performing media exchange into a chamber through another set of one or a plurality of inlets and one or a plurality of outlets.

14. The closed cells or organs culture system of claim 1, wherein images from cells or organs under culture or signals from other sensors or actuators are analyzed to control reagent constituents' delivery through machine vision or deep learning algorithms.

\* \* \* \* \*